(12) United States Patent  
Damon et al.

(10) Patent No.: US 7,700,637 B2
(45) Date of Patent: Apr. 20, 2010

(54) ORGANIC COMPOUNDS

(75) Inventors: Robert Edson Damon, Hopkinton, MA (US); Thalaththani Ralalage Vedananda, Shrewsbury, MA (US)

(73) Assignee: Novartis AG, Basel (CH)

(*) Notice: Subject to any disclaimer, the term of this patent is extended or adjusted under 35 U.S.C. 154(b) by 396 days.

(21) Appl. No.: 10/570,338

(22) PCT Filed: Sep. 16, 2004

(86) PCT No.: PCT/EP2004/010393

§ 371 (c)(1),
(2), (4) Date: Apr. 17, 2006

(87) PCT Pub. No.: WO2005/026134

PCT Pub. Date: Mar. 24, 2005

(65) Prior Publication Data

US 2007/0004704 A1    Jan. 4, 2007

Related U.S. Application Data

(60) Provisional application No. 60/503,950, filed on Sep. 17, 2003.

(51) Int. Cl.
*A61K 31/42* (2006.01)
*C07D 263/30* (2006.01)
(52) U.S. Cl. .................. 514/374; 548/235
(58) Field of Classification Search .......... 514/374; 548/235
See application file for complete search history.

(56) References Cited

U.S. PATENT DOCUMENTS

| | | | |
|---|---|---|---|
| 5,571,921 A | 11/1996 | Bender et al. | |
| 6,624,185 B2 | 9/2003 | Globik et al. | 514/374 |
| 6,884,812 B2 | 4/2005 | Globik et al. | 514/374 |
| 2003/0144332 A1 | 7/2003 | Glombik et al. | 514/374 |
| 2004/0068012 A1* | 4/2004 | Comess et al. | 514/562 |
| 2004/0122069 A1 | 6/2004 | Globik et al. | 514/374 |
| 2005/0267177 A1 | 12/2005 | Glombik et al. | 514/374 |

FOREIGN PATENT DOCUMENTS

| | | |
|---|---|---|
| EP | 1095930 | 5/2001 |
| EP | 1095930 B1 | 3/2003 |
| WO | 96/10559 A1 | 4/1996 |
| WO | 99/20275 A1 | 4/1999 |
| WO | 00/64876 A1 | 11/2000 |
| WO | WO 00/64876 | 11/2000 |
| WO | 04/000295 A1 | 12/2003 |
| WO | WO 2004/033419 | 4/2004 |

OTHER PUBLICATIONS

Database Chemicats Chemical Abstracts Service, Columbus, Ohio, US XP002312908 7902087/on & May 19, 2004, Chembridge Corporation, 16981 Via Tazon, Suite G, San Diego, CA 92127/USA.
Teixidor, et al., "Comparative Study of NS2(S-aryl) Pyridine-Based Dithia-Containing Ligands with Different Substituent Groups Reactivity toward Cu(II) and Ru(II)", Inorganic Chemistry, 2001, 40 (16), pp. 4010-4015.
Elwahy, et al., "Synthesis of New Benzo-substituted Macrocyclic Ligands Containing Pyridine or Triazole as Subcyclic Units", Tetrahedron, 2000, 56 (6), pp. 885-895.
Lucena, et al., "Synthesis and characterization of cyclopalladated and non-cyclopalladated complexes of ligands containing the 1,3-bis(thiomethyl)benzene unit", Polyhedron, 1996, 15 (18), pp. 3009-3018.

* cited by examiner

*Primary Examiner*—Taofiq A Solola
(74) *Attorney, Agent, or Firm*—Theresa Devlin

(57) ABSTRACT

Compounds of the formula

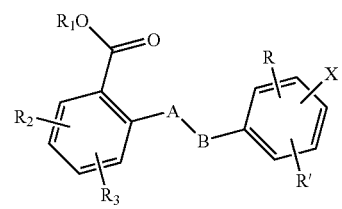

(I)

provide pharmacological agents which bind to Peroxisome Proliferator-Activated Receptors (PPARs). Accordingly, the compounds of the present invention are useful for the treatment of conditions mediated by the PPAR receptor activity in mammals. Such conditions include dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, inflammatory bowel diseases (IBDs), ulcerative colitis and Crohn's disease. The compounds of the present invention are particularly useful in mammals as hypoglycemic agents for the treatment and prevention of conditions in which impaired glucose tolerance, hyperglycemia and insulin resistance are implicated, such as type-1 and type-2 diabetes, and Syndrome X.

14 Claims, No Drawings

ORGANIC COMPOUNDS

This application claims benefit of U.S. Provisional Application 60/503,950, filed Sep. 17, 2003.

BACKGROUND

Compounds that bind to Peroxisome Proliferator-Activated Receptors (PPARs) are useful for the treatment of dyslipidemia, hyperlipidemia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, inflammatory bowel diseases, ulcerative colitis, Crohn's disease, hyperglycemia, insulin resistance, type-1 diabetes, type-2 diabetes, and Syndrome X.

BRIEF SUMMARY

The present invention provides compounds of the formula

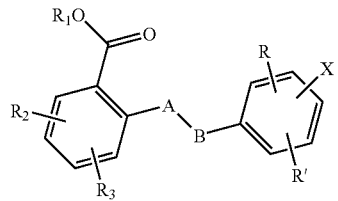

(I)

wherein
- $R_1$ is hydrogen, optionally substituted alkyl, aryl, heteroaryl, aralkyl or cycloalkyl;
- $R_2$ and $R_3$ are independently hydrogen, halogen, hydroxy, cyano, nitro, trifluoromethyl, optionally substituted alkyl, aryl, heteroaryl, aralkyl, heteroaralkyl, alkoxy, aryloxy, aralkoxy or heteroaralkoxy; or
- $R_2$ and $R_3$ combined together with the carbon atoms they are attached to form an optionally substituted fused 5- to 6-membered aromatic or heteroaromatic ring provided that $R_2$ and $R_3$ are attached to carbon atoms adjacent to each other;
- R and R' are independently hydrogen, halogen, optionally substituted alkyl, alkoxy, aralkyl or heteroaralkyl; or
- R and R' combined together with the carbon atoms to which they are attached form an optionally substituted fused 5- to 6-membered aromatic or heteroaromatic ring provided that R and R' are attached to carbon atoms adjacent to each other; or
- R—C and R'—C may independently be replaced by nitrogen;
- X is —Z—$(CH_2)_p$-Q-W in which
  - Z is a bond, O, S, S(O), $S(O)_2$, —C(O)— or —NHC(O)—; or
  - Z is —C(O)$NR_4$— in which
    - $R_4$ is hydrogen, alkyl or aralkyl;
  - p is an integer from 1 to 8;
  - Q is a bond or —C(O)—; or
  - Q is —O$(CH_2)_r$ or —S$(CH_2)_r$— in which
    - r is zero or an integer from 1 to 8; or
  - Q is —O$(CH_2)_{1-8}$O—, —S$(CH_2)_{1-8}$O— or —S$(CH_2)_{1-8}$S—; or
  - Q is —C(O)$NR_5$— in which
    - $R_5$ is hydrogen, optionally substituted alkyl, cycloalkyl, aryl, heteroaryl, aralkyl or heteroaralkyl; or
  - Q is —$NR_6$—, —$NR_6$C(O)—, —$NR_6$C(O)NH— or —$NR_6$C(O)O— in which
    - $R_6$ is hydrogen, lower alkyl or aralkyl;
  - W is cycloalkyl, aryl or heterocyclyl; or
  - W and $R_5$ taken together with the nitrogen atom to which they are attached form a fused 8- to 12-membered bicyclic ring, which may be optionally substituted or may contain another heteroatom selected from oxygen, nitrogen and sulfur; or
  - W is —[C$(R_7)_2]_s$-L in which
    - $R_7$ is hydrogen or lower alkyl;
    - s is an integer from 1 to 3;
    - L is aryl or heteroaryl;
- A-B is —NH—$S(O)_2$—; or
- A-B is —Y—C$(R_8)_2$ in which
  - Y is O or S;
  - $R_8$ is hydrogen or lower alkyl;

or a pharmaceutically acceptable salt thereof.

The compounds of the present invention bind to the Peroxisome Proliferator-Activated Receptors (PPARs) and, thus, the present invention provides pharmaceutical agents for the treatment of conditions mediated by the PPAR activity in mammals. Such conditions include dyslipidemia, hyperlipidemia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, inflammatory bowel diseases, ulcerative colitis and Crohn's disease. The compounds of the present invention are particularly useful in mammals as hypoglycemic agents for the treatment and prevention of conditions in which impaired glucose tolerance, hyperglycemia and insulin resistance are implicated such as type-1 and type-2 diabetes, and Syndrome X.

DETAILED DESCRIPTION

Listed below are definitions of various terms used to describe the compounds of the instant invention. These definitions apply to the terms as they are used throughout the specification unless they are otherwise limited in specific instances either individually or as part of a larger group, e.g., wherein an attachment point of a certain group is limited to a specific atom within that group, the point of attachment is defined by an arrow at the specific atom.

The term "optionally substituted alkyl" refers to unsubstituted or substituted straight or branched chain hydrocarbon groups having 1 to 20 carbon atoms, preferably 1 to 7 carbon atoms. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like. Substituted alkyl groups include, but are not limited to, alkyl groups substituted by one or more of the following groups: halo, hydroxy, cycloalkyl, alkanoyl, alkoxy, alkyloxyalkoxy, alkanoyloxy, amino, alkylamino, dialkylamino, alkanoylamino, thiol, alkylthio, alkylthiono, alkylsulfonyl, arylsulfonyl, heteroarylsulfonyl, sulfonamido, nitro, cyano, carboxy, alkoxycarbonyl, aryl, aralkoxy, guanidino, heterocyclyl including indolyl, imidazolyl, furyl, thienyl, thiazolyl, pyrrolidyl, pyridyl, pyrimidyl, piperidyl, morpholinyl and the like.

The term "lower alkyl" refers to those alkyl groups as described above having 1 to 7, preferably 1 to 4 carbon atoms.

The term "halogen" or "halo" refers to fluorine, chlorine, bromine and iodine.

The term "alkenyl" refers to any of the above alkyl groups having at least 2 carbon atoms and further containing at least one carbon to carbon double bond. Groups having two to four carbon atoms are preferred.

The term "alkynyl" refers to any of the above alkyl groups having at least two carbon atoms and further containing at least one carbon to carbon triple bond. Groups having two to four carbon atoms are preferred.

The term "alkylene" refers to a straight chain bridge of 1 to 6 carbon atoms connected by single bonds (e.g., —$(CH_2)_x$— wherein x is 1 to 6), which may be interrupted with one or more heteroatoms selected from oxygen, sulfur and nitrogen, and may be substituted with 1 to 3 substituents such as alkyl, alkoxy, halo, hydroxy, cycloalkyl, alkanoyl, alkyloxyalkoxy, alkanoyloxy, amino, alkylamino, dialkylamino, acylamino, carbamoyl, thiol, alkylthio, alkylthiono, sulfonyl, sulfonamido, sulfamoyl, nitro, cyano, carboxy, alkoxycarbonyl, aryl, aralkoxy, guanidino, heterocyclyl including indolyl, imidazolyl, furyl, thienyl, thiazolyl, pyrrolidyl, pyridyl, pyrimidyl, piperidyl, morpholinyl and the like The term "cycloalkyl" refers to optionally substituted monocyclic, bicyclic or tricyclic hydrocarbon groups of 3 to 12 carbon atoms, each of which may optionally be substituted by one or more substituents such as alkyl, halo, oxo, hydroxy, alkoxy, alkanoyl, amino, alkylamino, dialkylamino, thiol, alkylthio, nitro, cyano, carboxy, carboxyalkyl, alkoxycarbonyl, alkyl- and arylsulfonyl, sulfonamido, heterocyclyl and the like.

Exemplary monocyclic hydrocarbon groups include but are not limited to cyclopropyl, cyclobutyl, cyclopentyl, cyclopentenyl, cyclohexyl and cyclohexenyl and the like.

Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like.

Exemplary tricyclic hydrocarbon groups include adamantyl and the like.

The term "alkoxy" refers to alkyl-O—.

The term "acyl" refers to alkanoyl, aroyl, heteroaroyl, arylalkanoyl and the like.

The term "alkanoyl" refers to alkyl-C(O)—.

The term "alkanoyloxy" refers to alkyl-C(O)—O—.

The terms "alkylamino" and "dialkylamino" refer to alkyl-NH— and (alkyl)$_2$N—, respectively.

The term "alkanoylamino" refers to alkyl-C(O)—NH—.

The term "alkylthio" refers to alkyl-S—.

The term "alkylaminothiocarbonyl" refers to alkyl-NHC(S)—.

The term "trialkylsilyl" refers to (alkyl)$_3$Si—.

The term "trialkylsilyloxy" refers to (alkyl)$_3$SiO—.

The term "alkylthiono" refers to alkyl-S(O)—.

The term "alkylsulfonyl" refers to alkyl-S(O)$_2$—.

The term "alkoxycarbonyl" refers to alkyl-O—C(O)—.

The term "alkoxycarbonyloxy" refers to alkyl-O—C(O)O—.

The term "carbamoyl" refers to alkyl-NH—C(O)—, (alkyl)$_2$N—C(O)—, aryl-NH—C(O)—, alkyl(aryl)-N—C(O)—, heteroaryl-NH—C(O)—, alkyl(heteroaryl)-N—C(O)—, aralkyl-NH—C(O)— and alkyl(aralkyl)-N—C(O)—.

The term "aryl" refers to monocyclic or bicyclic aromatic hydrocarbon groups having 6 to 12 carbon atoms in the ring portion, such as phenyl, naphthyl, tetrahydronaphthyl, biphenyl and diphenyl groups, each of which may optionally be substituted by one to four substituents such as alkyl, halo, hydroxy, alkoxy, alkanoyl, alkanoyloxy, optionally substituted amino, thiol, alkylthio, nitro, cyano, carboxy, carboxyalkyl, alkoxycarbonyl, alkylthiono, alkyl- and arylsulfonyl, sulfonamido, heterocycloyl and the like.

The term "monocyclic aryl" refers to phenyl as described under aryl.

The term "aralkyl" refers to an aryl group bonded directly through an alkyl group, such as benzyl.

The term "aralkylthio" refers to aralkyl-S—.

The term "aralkoxy" refers to an aryl group bonded directly through an alkoxy group.

The term "arylsulfonyl" refers to aryl-S(O)$_2$—.

The term "arylthio" refers to aryl-S—.

The term "aroyl" refers to aryl-C(O)—.

The term "aroylamino" refers to aryl-C(O)—NH—.

The term "arylcarbonyl" refers to aryl-O—C(O)—.

The term "heterocyclyl" or "heterocyclo" refers to an optionally substituted, fully saturated or unsaturated, aromatic or nonaromatic cyclic group, for example, which is a 4- to 7-membered monocyclic, 7- to 12-membered bicyclic, or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, dihydroidolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl" includes substituted heterocyclic groups. Substituted heterocyclic groups refer to heterocyclic groups substituted with 1, 2 or 3 substituents which are selected from the group consisting of:

| (a) | alkyl; |
|---|---|
| (b) | hydroxy (or protected hydroxy); |
| (c) | halo; |
| (d) | oxo (i.e. =O); |
| (e) | optionally substituted amino, alkylamino or dialkylamino; |
| (f) | alkoxy; |
| (g) | cycloalkyl; |

| | -continued |
|---|---|
| (h) | carboxy; |
| (i) | heterocyclooxy; |
| (j) | alkoxycarbonyl, such as unsubstituted lower alkoxycarbonyl; |
| (k) | mercapto; |
| (l) | nitro; |
| (m) | cyano; |
| (n) | sulfonamido, sulfonamidoalkyl, sulfonamidoaryl or sulfonamidodialkyl; |
| (o) | alkylcarbonyloxy; |
| (p) | arylcarbonyloxy; |
| (q) | arylthio; |
| (r) | aryloxy; |
| (s) | alkylthio; |
| (t) | formyl; |
| (u) | carbamoyl; |
| (v) | aralkyl; and |
| (w) | aryl substituted with alkyl, cycloalkyl, alkoxy, hydroxy, amino, alkylamino, dialkylamino or halo. |

The term "heterocyclooxy" denotes a heterocyclic group bonded through an oxygen bridge.

The term "heteroaryl" refers to an aromatic heterocycle, for example monocyclic or bicyclic aryl, such as pyrrolyl, pyrazolyl, imidazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl, and the like, optionally substituted by e.g. lower alkyl, lower alkoxy or halo.

The term "heteroarylsulfonyl" refers to heteroaryl-$S(O)_2$—.

The term "heteroaroyl" refers to heteroaroyl-$C(O)$—.

The term "heteroaralkyl" refer to a heteroaryl group bonded through an alkyl group.

Pharmaceutically acceptable salts of any compound of the present invention refer to salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris(hydroxymethyl)-methyl-ammonium salts, and salts with amino acids.

Similarly acid addition salts, such as those formed with mineral acids, organic carboxylic acids and organic sulfonic acids e.g. hydrochloric acid, maleic acid and methanesulfonic acid, are possible provided a basic group, such as pyridyl, constitutes part of the structure.

Prodrug derivatives of any compound of the invention are derivatives of said compounds which following administration release the parent compound in vivo via some chemical or physiological process, e.g., a prodrug on being brought to the physiological pH or through enzyme action is converted to the parent compound. Exemplary prodrug derivatives are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono or disubstituted lower alkyl esters such as the (amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester, and the like conventionally used in the art.

As described herein above, the present invention provides benzoic acid derivatives of formula (I), pharmaceutical compositions containing them, methods for preparing such compounds and methods of treating conditions mediated by the PPAR activity by administration of a therapeutically effective amount of a compound of the present invention or a pharmaceutical composition thereof.

Preferred are the compounds of formula (I) having the formula

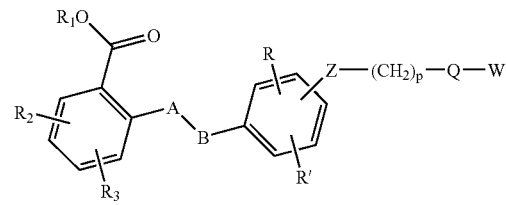

(IA)

wherein
$R_1$ is hydrogen or optionally substituted alkyl;
$R_2$ and $R_3$ are independently hydrogen, halogen, trifluoromethyl, optionally substituted lower alkyl, alkoxy, aryl or heteroaryl; or
$R_2$ and $R_3$ combined together with the carbon atoms they are attached to form an optionally substituted fused 5- to 6-membered aromatic or heteroaromatic ring provided that
$R_2$ and $R_3$ are attached to carbon atoms adjacent to each other;
R and R' are independently hydrogen, halogen, optionally substituted $C_{1-6}$ alkyl, $C_{1-6}$ alkoxy, aralkyl or heteroaralkyl;
Z is a bond, O, S or —NHC(O)—; or
Z is —C(O)$NR_4$— in which
$R_4$ is hydrogen, alkyl or aralkyl;
p is an integer from 1 to 5;
Q is a bond or —C(O)—; or
Q is —O(CH$_2$)$_r$ or —S(CH$_2$)$_r$ in which
r is zero or an integer from 1 to 3; or
Q is —C(O)$NR_5$— in which
$R_5$ is hydrogen, optionally substituted alkyl, cycloalkyl, aryl, heteroaryl, aralkyl or heteroaralkyl; or
Q is —$NR_6$—, —$NR_6$C(O)—, —$NR_6$C(O)NH— or —$NR_6$C(O)O— in which
$R_6$ is hydrogen, lower alkyl or aralkyl;
W is cycloalkyl, aryl or heterocyclyl; or
W and $R_5$ taken together with the nitrogen atom to which they are attached form a fused 8- to 12-membered bicyclic ring, which may be optionally substituted or may contain another heteroatom selected from oxygen, nitrogen and sulfur; or
W is —[C(R$_7$)$_2$]$_s$-L in which
$R_7$ is hydrogen or lower alkyl;
s is an integer from 1 to 3;
L is aryl or heteroaryl;
A-B is —NH—S(O)$_2$—; or
A-B is —Y—C(R$_8$)$_2$— in which
Y is O or S;
$R_8$ is hydrogen or lower alkyl;

or a pharmaceutically acceptable salt thereof.
Preferred are the compounds of formula (IA) wherein
$R_1$ is hydrogen or optionally substituted alkyl;

$R_2$ and $R_3$ are independently hydrogen, halogen, trifluoromethyl, optionally substituted lower alkyl, alkoxy, aryl or heteroaryl; or $R_2$ and $R_3$ combined together with the carbon atoms they are attached to form an optionally substituted fused 6-membered aromatic ring provided that $R_2$ and $R_3$ are attached to carbon atoms adjacent to each other;

R is hydrogen, halogen, optionally substituted $C_{1-6}$ alkyl or $C_{1-6}$ alkoxy;

R' is hydrogen;

Z is a bond, O or S;

p is an integer from 1 to 5;

Q is a bond; or

Q is —O(CH$_2$)$_r$— or —S(CH$_2$)$_r$— in which
r is zero or 1; or

Q is —C(O)NR$_5$— in which
$R_5$ is hydrogen, optionally substituted alkyl, cycloalkyl, aryl or heteroaryl; or Q is —NR$_6$—, —NR$_6$C(O), —NR$_6$C(O)NH— or —NR$_6$C(O)O— in which
$R_6$ is hydrogen, alkyl or aralkyl;

W is cycloalkyl, aryl or heterocyclyl; or

W is —[C(R$_7$)$_2$]$_s$-L in which
$R_7$ is hydrogen or lower alkyl;
s is an integer from 1 to 2;
L is aryl;

A-B is —NH—S(O)$_2$—; or

A-B is —Y—C(R$_8$)$_2$— in which
Y is O or S;
$R_8$ is hydrogen or methyl;

or a pharmaceutically acceptable salt thereof.

Further preferred are the compounds of formula (IA) having the formula

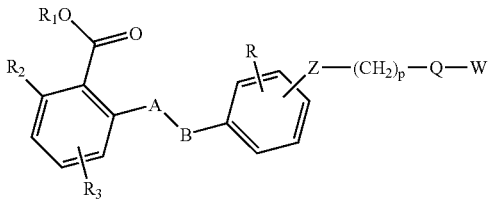

(IB)

wherein
$R_1$ is hydrogen or optionally substituted alkyl;
$R_2$ and $R_3$ are independently hydrogen, halogen, trifluoromethyl, lower alkyl, lower alkoxy or aryl;
R is hydrogen, halogen, optionally substituted $C_{1-6}$ alkyl or $C_{1-6}$ alkoxy;
Z is a bond, O or S;
p is an integer from 1 to 5;
Q is a bond; or
Q is —O(CH$_2$)$_r$ or —S(CH$_2$)$_r$ in which
r is zero; or
Q is —C(O)NR$_5$— in which
$R_5$ is hydrogen, optionally substituted alkyl or cycloalkyl; or
Q is —NR$_6$—, —NR$_6$C(O)—, —NR$_6$C(O)NH— or —NR$_6$C(O)O— in which
$R_6$ is hydrogen or alkyl;
W is cycloalkyl, aryl or heterocyclyl; or
W is —[C(R$_7$)$_2$]$_s$-L in which
$R_7$ is hydrogen or lower alkyl;
s is 1;
L is aryl;

A-B is —NH—S(O)$_2$—; or
A-B is —Y—C(R$_8$)$_2$— in which
Y is O or S;
$R_8$ is hydrogen or methyl;

or a pharmaceutically acceptable salt thereof.

Preferred are the compounds of formula (IB) having the formula

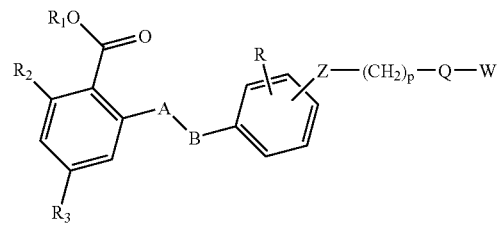

(IC)

wherein
$R_1$ is hydrogen or optionally substituted lower alkyl;
$R_2$ and $R_3$ are independently hydrogen, halogen, lower alkyl or lower alkoxy;
R is hydrogen;
Z is a bond, O or S;
p is an integer from 1 to 4;
Q is a bond, O or S; or
Q is —NR$_6$C(O)— in which
$R_6$ is hydrogen or lower alkyl;
W is cycloalkyl, aryl or heterocyclyl; or
W is —[C(R$_7$)$_2$]$_s$-L in which
$R_7$ is hydrogen or methyl;
s is 1;
L is aryl;
A-B is —NH—S(O); or
A-B is —Y—C(R$_8$)$_2$— in which
Y is O or S;
$R_8$ is hydrogen or methyl;

or a pharmaceutically acceptable salt thereof.

Preferred are the compounds of formula (IC) wherein
$R_1$ and $R_3$ are hydrogen;
$R_2$ is hydrogen, fluoro, chloro, $C_{1-6}$ alkyl or $C_{1-3}$ alkoxy;

or a pharmaceutically acceptable salt thereof.

Preferred are also the compounds of formula (IC) wherein
$R_1$ is hydrogen;
$R_2$ is hydrogen, fluoro, chloro, $C_{1-3}$ alkyl or $C_{1-4}$ alkoxy;
$R_3$ is fluoro, chloro, $C_{1-3}$ alkyl, $C_{1-3}$ alkoxy or phenyl;

or a pharmaceutically acceptable salt thereof.

Preferred are also the compounds of formula (IC) wherein
$R_1$ is hydrogen or optionally substituted lower alkyl;
$R_2$ and $R_3$ are independently hydrogen, halogen, lower alkyl or lower alkoxy;
Z is a bond;
p is an integer of 1 or 2;
Q is —NR$_6$C(O)— in which
$R_6$ is hydrogen or methyl;
W is —C(R$_7$)$_z$-L in which
$R_7$ is hydrogen or methyl;
L is aryl;
A-B is —NH—S(O)$_2$—; or
A-B is —Y—C(R$_8$)$_2$—, in which
Y is O;
$R_8$ is hydrogen or methyl;

or a pharmaceutically acceptable salt thereof.

Preferred are also the compounds of formula (IC), designated as the A group, wherein
R₁ is hydrogen or optionally substituted lower alkyl;
R₂ and R₃ are independently hydrogen, halogen, lower alkyl or lower alkoxy;
Z is a bond, O or S;
p is an integer of 2 or 3;
Q is O or S;
W is aryl, heterocyclyl or heteroaralkyl;
A-B is —NH—S(O)₂—; or
A-B is —O—C(R₈)₂— in which
  Y is O or S;
  R₈ is hydrogen or methyl;
or a pharmaceutically acceptable salt thereof.

Preferred are the compounds in the A group wherein
W is selected from the group consisting of:

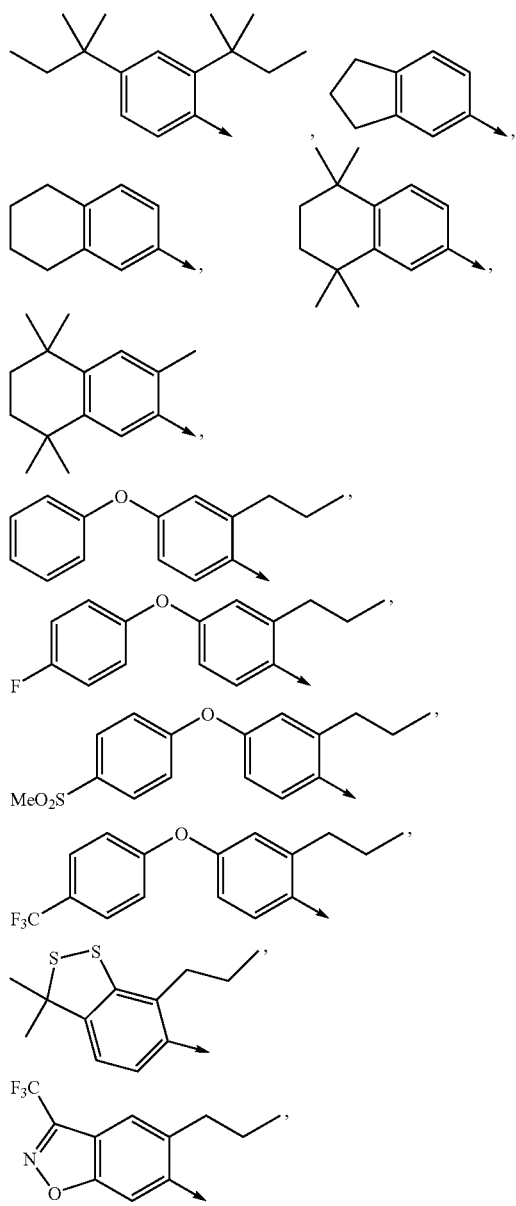

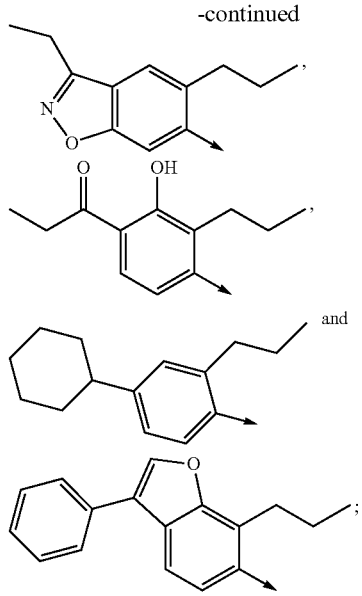

or a pharmaceutically acceptable salt thereof.

Preferred are also the compounds of formula (IC), designated as the B group, wherein
R₁ is hydrogen or optionally substituted lower alkyl;
R₂ and R₃ are independently hydrogen, halogen, lower alkyl or lower alkoxy;
Z is O or S;
p is an integer of 1 or 2;
Q is a bond;
W is aryl, heterocyclyl or heteroaralkyl;
A-B is —NH—S(O)₂—; or
A-B is —Y—C(R₈)₂— in which
  Y is O or S;
  R₈ is hydrogen or methyl;
or a pharmaceutically acceptable salt thereof.

Preferred are the compounds in the B group wherein
W is selected from the group consisting of:

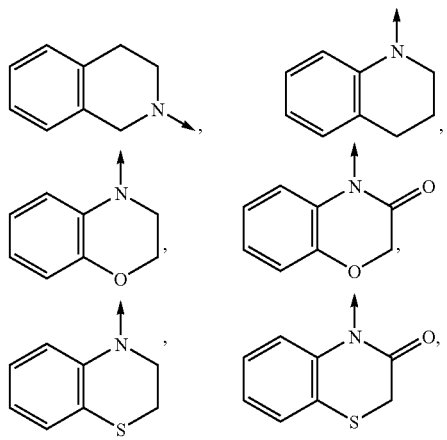

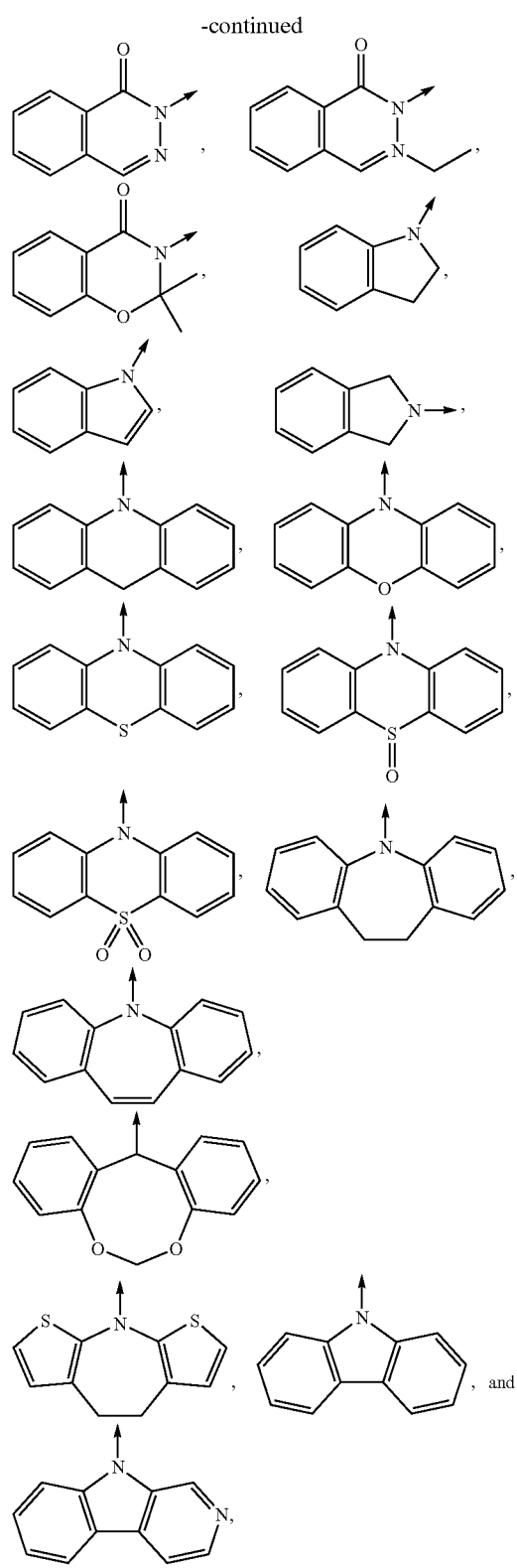
or a pharmaceutically acceptable salt thereof.
Preferred are also the compounds in the B group, designated as the C group, wherein
A-B is —NH—S(O)$_2$—;
or a pharmaceutically acceptable salt thereof.
Preferred are the compounds in the C group wherein W is selected from the group consisting of:
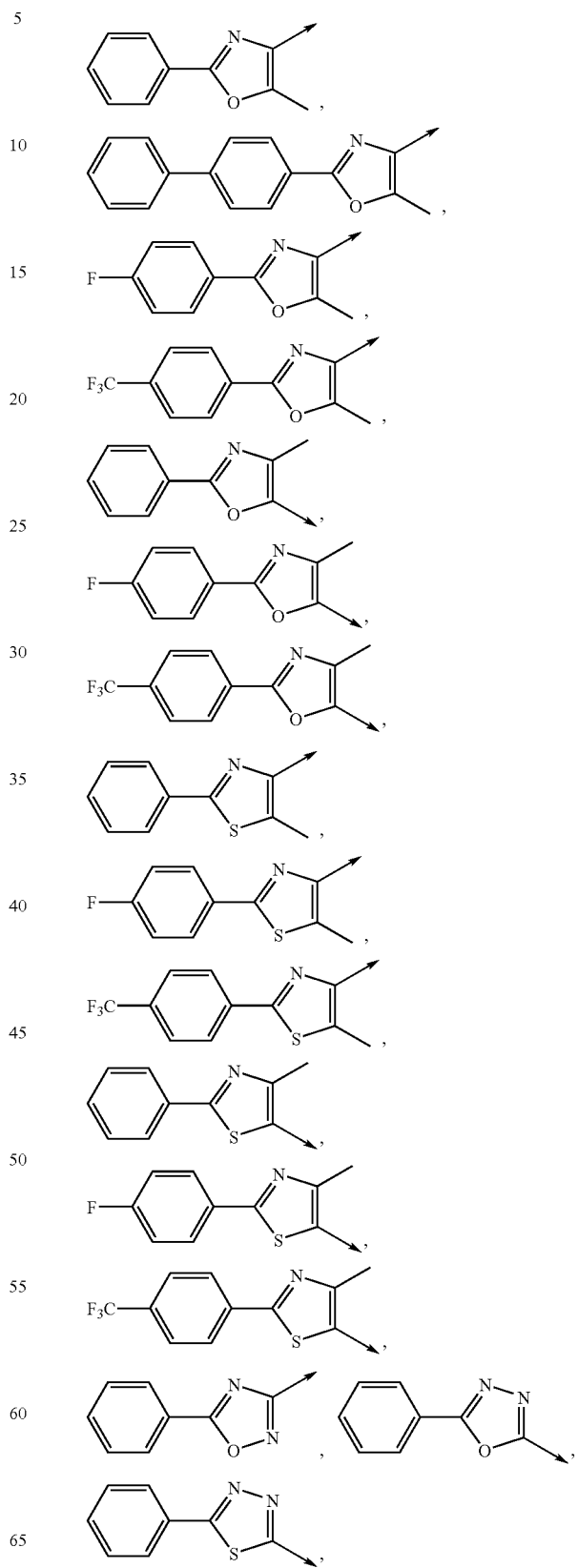

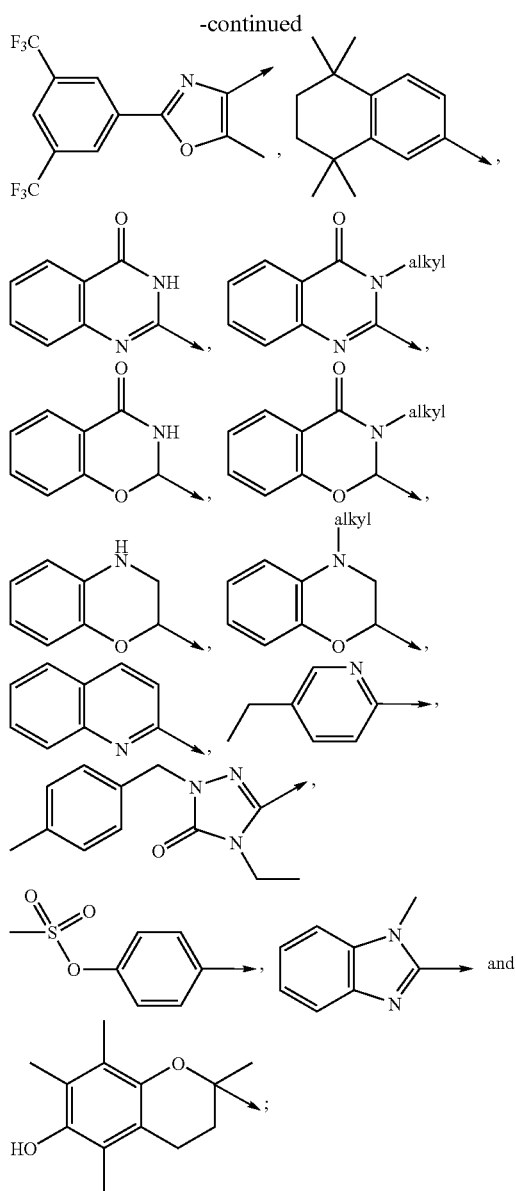

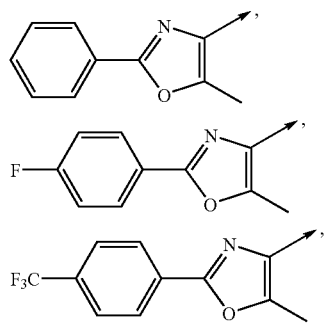

or a pharmaceutically acceptable salt thereof.

Further preferred are the compounds in the C group wherein

W is selected from the group consisting of:

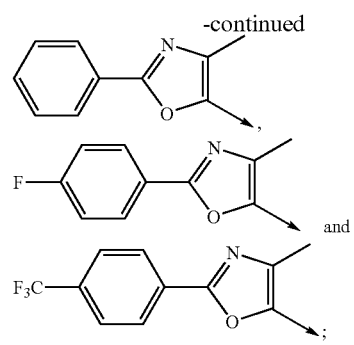

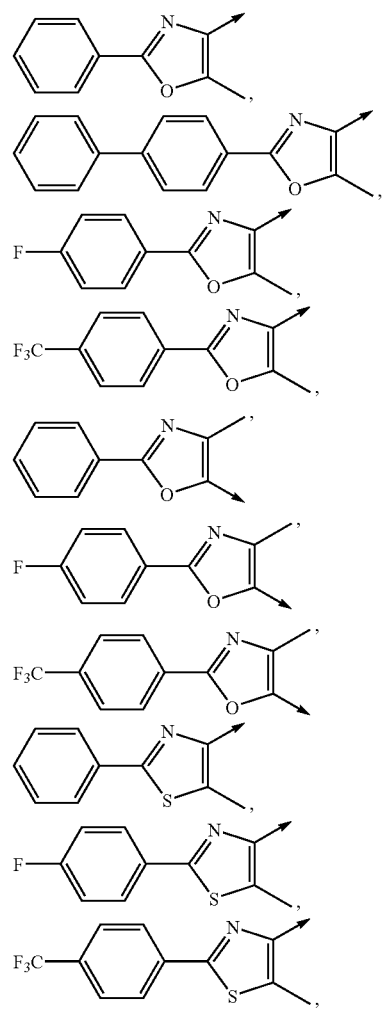

or a pharmaceutically acceptable salt thereof.

Preferred are also the compounds in the B group, designated as the D group, wherein A-B is —Y—C(R$_8$)$_2$— in which
Y is O;
R$_5$ is hydrogen;

or a pharmaceutically acceptable salt thereof.

Preferred are the compounds in the D group wherein
W is selected from the group consisting of:

-continued

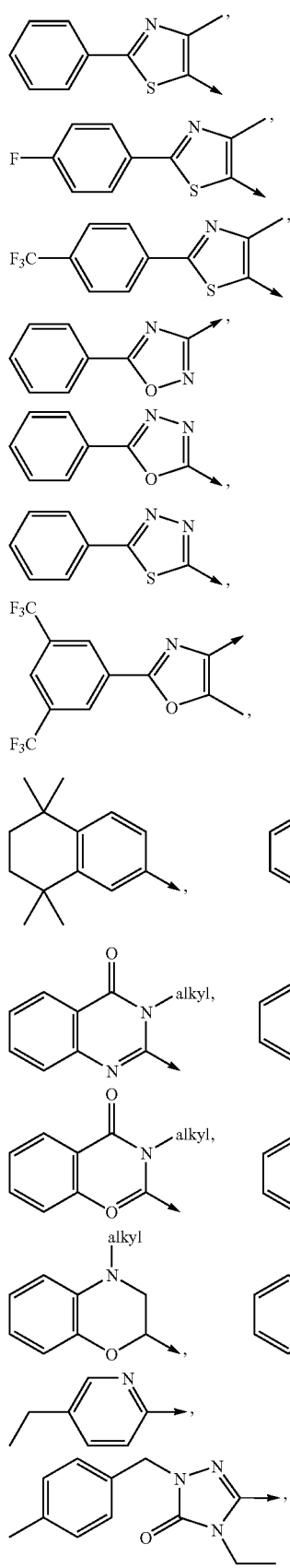

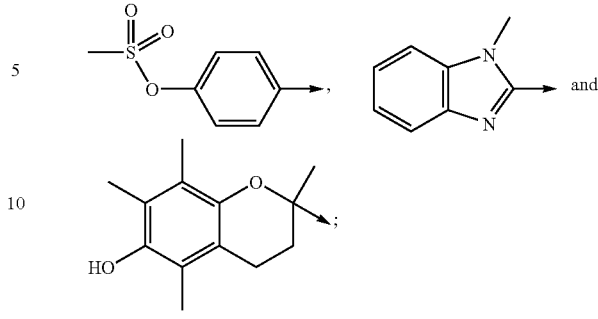

or a pharmaceutically acceptable salt thereof.

Further preferred are the compounds in the D group wherein

W is selected from the group consisting of:

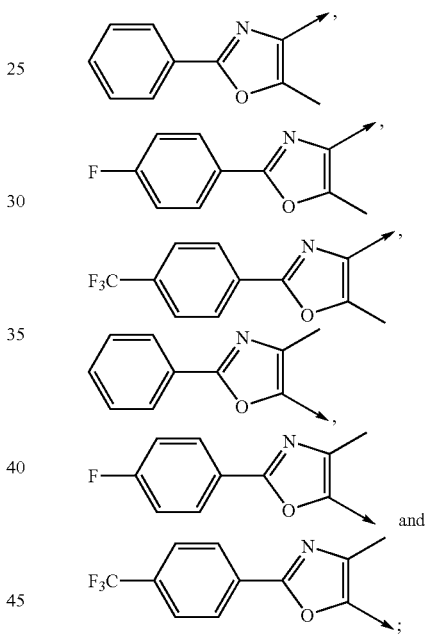

or a pharmaceutically acceptable salt thereof.

Particular embodiments of the invention are:
6-Methyl-2-[4-(5-methyl-2-phenyl-oxazol-4-ylmethoxy)-benzenesulfonylamino]-benzoic acid;
6-Chloro-2-[4-(5-methyl-2-phenyl-oxazol-4-ylmethoxy)-benzenesulfonylamino]-benzoic acid;
3-[4-(5-Methyl-2-phenyl-oxazol-4-ylmethoxy)-benzene-sulfonylamino]-biphenyl-4-carboxylic acid;
4-Chloro-2-{4-[5-methyl-2-(4-trifluoromethyl-phenyl)-oxazol-4-ylmethoxy]-benzene-sulfonylamino}benzoic acid;
6-Fluoro-2-[4-(5-methyl-2-phenyl-oxazol-4-ylmethoxy)-benzenesulfonylamino]-benzoic acid;
4-Chloro-2-{4-[2-(4-fluoro-phenyl)-5-methyl-oxazol-4-yl-methoxy]-benzenesulfonylamino}-benzoic acid;
2-[4-(5-Methyl-2-phenyl-oxazol-4-ylmethoxy)-benzene-sulfonylamino]-6-trifluoromethyl-benzoic acid;
4-Chloro-2-[4-(5-methyl-2-phenyl-oxazol-4-ylmethoxy)-benzenesulfonylamino]-benzoic acid;

3,5-Dimethyl-2-[4-(5-methyl-2-phenyl-oxazol-4-yl-methoxy)-benzenesulfonylamino]-benzoic acid;
2-{4-[5-Methyl-2-(4-trifluoromethyl-phenyl)-oxazol-4-yl-methoxy]-benzenesulfonylamino}-benzoic acid;
2-{4-[2-(4-Fluoro-phenyl)-5-methyl-oxazol-4-ylmethoxy]-benzenesufonylamino}benzoic acid;
2-[4-(5-Methyl-2-phenyl-oxazol-4-ylmethylsulfanyl)-benzenesulfonylamino]-benzoic acid;
4-Fluoro-2-[4-(5-methyl-2-phenyl-oxazol-4-ylmethoxy)-benzenesulfonylamino]-benzoic acid;
2-[4-(5-Methyl-2-phenyl-oxazol-4-ylmethoxy)-benzenesulfonylamino]-benzoic acid;
4-Methyl-2-[4-(5-methyl-2-phenyl-oxazol-4-ylmethoxy)-benzenesulfonylamino]-benzoic acid;
4,5-Difluoro-2-[4-(5-methyl-2-phenyl-oxazol-4-yl-methoxy)-benzenesulfonylamino]-benzoic acid;
6-Methoxy-2-[4-(5-methyl-2-phenyl-oxazol-4-ylmethoxy)-benzenesulfonylamino]-benzoic acid;
5-Fluoro-2-[4-(5-methyl-2-phenyl-oxazol-4-ylmethoxy)-benzenesulfonylamino]-benzoic acid;
5-Chloro-2-[4-(5-methyl-2-phenyl-oxazol-4-ylmethoxy)-benzenesulfonylamino]-benzoic acid;
3-[4-(5-Methyl-2-phenyl-oxazol-4-ylmethoxy)-benzenesulfonylamino]-naphthalene-2-carboxylic acid;
5-Methoxy-2-[4-(5-methyl-2-phenyl-oxazol-4-ylmethoxy)-benzenesulfonylamino]-benzoic acid;
5-Methyl-2-[4-(5-methyl-2-phenyl-oxazol-4-ylmethoxy)-benzenesulfonylamino]-benzoic acid;
5-Acetylamino-2-[4-(5-methyl-2-phenyl-oxazol-4-yl-methoxy)-benzenesulfonylamino]-benzoic acid;
4,5-Dimethoxy-2-[4-(5-methyl-2-phenyl-oxazol-4-yl-methoxy)-benzenesulfonylamino]-benzoic acid;
4-Chloro-2-{4-[2-(5-methyl-2-phenyl-oxazol-4-yl)-ethoxy]-benzenesulfonylamino}-benzoic acid;
3-{4-[2-(5-Methyl-2-phenyl-oxazol-4-yl)-ethoxy]-benzenesulfonylamino}-biphenyl-4-carboxylic acid;
2,3-Dimethoxy-6-{4-[2-(5-methyl-2-phenyl-oxazol-4-yl)-ethoxy]-benzenesulfonyl-amino}benzoic acid;
2-{4-[2-(5-Methyl-2-phenyl-oxazol-4-yl)-ethoxy]-benzenesulfonylamino}-benzoic acid;
2-{4-[2-(5-Methyl-2-phenyl-oxazol-4-yl)-ethylsulfanyl]-benzenesulfonylamino}-benzoic acid;
2-[4-(4-Trifluoromethyl-benzylcarbamoyl)-benzenesulfonylamino]-benzoic acid;
2-Methyl-6-[4-(5-methyl-2-phenyl-oxazol-4-ylmethoxy)-benzyloxy]-4-propoxy-benzoic acid methyl ester;
4-Chloro-2-{4-[2-(5-methyl-2-phenyl-oxazol-4-yl)-ethoxy]-benzyloxy}-benzoic acid ethyl ester;
4-Methoxy-2-{4-[2-(5-methyl-2-phenyl-oxazol-4-yl)-ethoxy]-benzyloxy}benzoic acid;
3-{4-[2-(5-Methyl-2-phenyl-oxazol-4-yl)-ethoxy]-benzyloxy}naphthalene-2-carboxylic acid;
2-Methyl-6-{4-[2-(5-methyl-2-phenyl-oxazol-4-yl)-ethoxy]-benzyloxy}-4-propoxy-benzoic acid methyl ester;
2-{4-[2-(5-Methyl-2-phenyl-oxazol-4-yl)-ethoxy]-benzyloxy}-4-propoxy-benzoic acid;
4-Methyl-2-{4-[2-(5-methyl-2-phenyl-oxazol-4-yl)-ethoxy]-benzyloxy}-benzoic acid;
4-Chloro-2-[3-(5-methyl-2-phenyl-oxazol-4-ylmethoxy)-benzyloxy]-benzoic acid;
4-Chloro-2-[3-(5-methyl-2-phenyl-oxazol-4-ylmethoxymethyl)-benzyloxy]-benzoic acid;
2,4-Dimethoxy-6-{4-[2-(5-methyl-2-phenyl-oxazol-4-yl)-ethoxy]-benzyloxy}-benzoic acid;
2-Methyl-6-{4-[2-(5-methyl-2-phenyl-oxazol-4-yl)-ethoxy]-benzloxy}-propoxy-benzoic acid;
4-Isopropoxy-2-methyl-6-{3-[2-(5-methyl-2-phenyl-oxazol-4-yl)-ethoxy]-benzyloxy}-benzoic acid;
2,4-Dimethoxy-6-[4-(5-methyl-2-phenyl-oxazol-4-yl-methoxy)-benzyloxy]-benzoic acid;
2-Methyl-6-[4-(5-methyl-2-phenyl-oxazol-4-ylmethoxy)-benzyloxy]-4-propoxy-benzoic acid;
2-{4-[2-(5-Methyl-2-phenyl-oxazol-4-yl)-ethoxy]-benzyloxy}-4,6-bis-trifluoromethyl-benzoic acid;
2-[4-(5-Methyl-2-phenyl-oxazol-4-ylmethoxy)-benzyloxy]-4,6-bis-trifluoromethyl-benzoic acid;
2-Fluoro-6-[4-(5-methyl-2-phenyl-oxazol-4-ylmethoxy)-benzyloxy]-benzoic acid;
4-Isopropoxy-2-methyl-6-{4-[2-(5-methyl-2-phenyl-oxazol-4-yl)-ethoxy]-benzyloxy}-benzoic acid;
2-Fluoro-6-{4-[2-(5-methyl-2-phenyl-oxazol-4-yl)-ethoxy]-benzyloxy}-benzoic acid;
2-Methoxy-6-[4-(5-methyl-2-phenyl-oxazol-4-ylmethoxy)-benzyloxy]-benzoic acid;
2-Methoxy-6-{4-[2-(5-methyl-2-phenyl-oxazolyl)-ethoxy]-benzyloxy}-benzoic acid;
4-Chloro-2-[4-(5-methyl-2-phenyl-oxazol-4-ylmethoxy)-benzyloxy]-benzoic acid;
4-Chloro-2-{4-[2-(5-methyl-2-phenyl-oxazol-4-yl)-ethoxy]-benzyloxy}benzoic acid;
4-sec-Butoxy-2-(4-{2-[2-(4-fluoro-phenyl)-5-methyl-oxazol-4-yl]-ethoxy}-benzloxy)-6-methyl-benzoic acid;
4-Fluoro-2-(4-{2-[2-(4-fluoro-phenyl)-5-methyl-oxazol-4-yl]-ethoxy}-benzloxy)-6-isopropoxy-benzoic acid;
4-Fluoro-2-(4-{2-[2-(4-fluoro-phenyl)-5-methyl-oxazol-4-yl]-ethoxy}-benzyloxy)-6-propoxy-benzoic acid;
2-(4-{2-[2-(4-Fluoro-phenyl)-5-methyl-oxazol-4-yl]-ethoxy}-benzyloxy)-4-isopropoxy-6-methyl-benzoic acid;
4-Isopropoxy-2-methyl-6-(4-{2-[5-methyl-2-(4-trifluoromethyl-phenyl)-oxazol-4-yl]-ethoxy}-benzyloxy)-benzoic acid;
2-(4-{2-[2-(4-Fluoro-phenyl)-5-methyl-oxazol-4-yl]-ethoxy}-benzyloxy)-6-methyl-4-(tetrahydro-furan-3-yloxy)-benzoic acid;
4-Chloro-2-[4-(5-methyl-2-phenyl-oxazol-4-ylmethoxymethyl)-benzyloxy]-benzoic acid;
4-Chloro-2-(3-{[(4-methyl-2-phenyl-thiazole-5-carbonyl)-amino]-methyl}-benzyloxy)-benzoic acid;
4-Isopropoxy-2-methyl-6-[3-({methyl-[2-(4-trifluoromethyl-phenyl)-acetyl]-amino}-methyl)-benzyloxy]-benzoic acid;
2-[3-({Ethyl-[2-(4-trifluoromethyl-phenyl)-acetyl]-amino}-methyl)-benzyloxy]-4 isopropoxy-6-methyl-benzoic acid;
2-[3-({[2-(4-Chloro-phenyl)-acetyl]-methyl-amino}-methyl)-benzyloxy]-4-isopropoxy-6-methyl-benzoic acid;
4-Isopropoxy-2-methyl-6-(3-{[methyl-(2-p-tolyl-acetyl)-amino]-methyl}-benzyloxy)-benzoic acid;
2-(3-{[(2-Benzo[1,3]dioxol-5-yl-acetyl)-methyl-amino]-methyl}-benzyloxy)-4-isopropoxy-6-methyl-benzoic acid; and
4-Isopropoxy-2-methyl-6-{3-[(methyl-phenylacetyl-amino]methyl-benzyloxy}-benzoic acid;

or a pharmaceutically acceptable salt thereof.

The compounds of the invention depending on the nature of the substituents, may possess one or more asymmetric centers. The resulting diastereoisomers, enantiomers and geometric isomers are also encompassed by the instant invention.

Compounds of formula (I) wherein A-B represents —NH—S(O)$_2$— may be prepared starting from sulfonic acid analogs of the formula

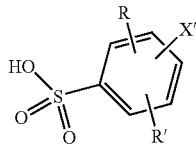
(1)

or cationic salts thereof, in which R and R' have meanings as defined herein, X' represents X as defined herein, or X' is a group convertible to X, i.e., compounds of formula (1) may be first treated with a chlorinating agent such as thionyl chloride or oxalyl chloride to form sulfonyl chlorides of the formula

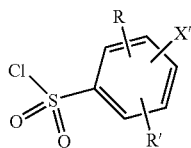
(2)

wherein R, R' and X' have meanings as defined herein above, using reaction conditions described herein, or using conditions well known in the art. Sulfonic acids of formula (1) may be obtained by methods described herein or modifications thereof, or by methods known in the art.

Sulfonyl chlorides of formula (2) wherein R, R' and X' have meanings as defined herein above may then be reacted with amines of the formula

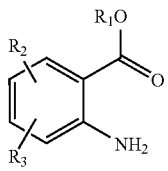
(3)

in which R$_1$, R$_2$ and R$_3$ have meanings as defined herein, in the presence of a base such as triethylamine (TEA), diisopropylethylamine (DIEA), N-methylmorpholine (NMM) or pyridine in an inert solvent such as dichloromethane (DCM), N,N-dimethylformamide (DMF) or tetrahydrofuran (THF) to obtain compounds of the formula

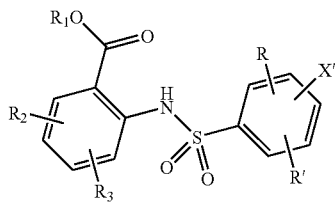
(Ia)

wherein R$_1$, R$_2$, R$_3$, R and R' have meanings as defined herein, and X' represents X as defined herein, or X' is a group convertible to X. Amines of formula (3) may be obtained by methods described herein or modifications thereof, or by methods known in the art.

Compounds of formula (Ia) wherein X' represents X as defined herein may be obtained from compounds of formula (Ia) wherein X' is a group convertible to X using methods described herein or modifications thereof, or using methods well known in the art. For example, compounds of formula (Ia) in which X' is benzyloxy can be first converted to compounds of the formula

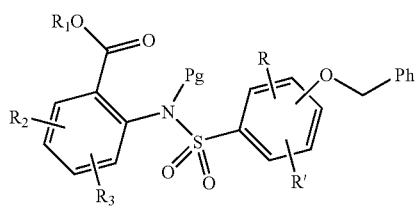
(4)

wherein R$_1$, R$_2$, R$_3$, R and R' have meanings as defined herein above, and Pg represents a protecting group such as t-butoxycarbonyl using methods described herein or modifications thereof, or using methods well known in the art, e.g., compounds of formula (Ia) wherein X' is benzyloxy may be converted to compounds of formula (4) wherein Pg is t-butoxycarbonyl by treatment with di-t-butyl dicarbonate and a base such as TEA or dimethylaminopyridine (DMAP), or combinations thereof, in an organic solvent such as DMF or THF.

Compounds of formula (4) wherein Pg represents a protecting group such as t-butoxycarbonyl can then be converted to compounds of the formula

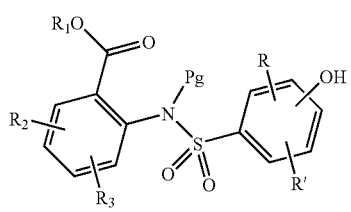
(5)

wherein R$_1$, R$_2$, R$_3$, R and R' have meanings as defined herein, e.g., by reduction with hydrogen in the presence of a catalyst such as palladium on carbon in a polar organic solvent such as ethyl acetate (EtOAc) or ethanol. The resulting phenols of formula (5) may then be treated with an alkylating agent of the formula

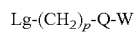
Lg-(CH$_2$)$_p$-Q-W (6)

wherein p, Q and W have meanings as defined herein and Lg represents a leaving group such as iodide, bromide, chloride, methanesulfonate or trifluoromethanesulfonate, in the presence of a base such as cesium carbonate, potassium carbonate or sodium hydride in an inert solvent such as DMF or THF to form compounds of the formula

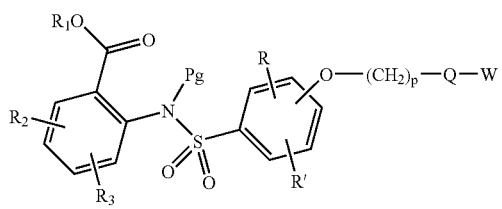
(7)

wherein R$_1$, R$_2$, R$_3$, R, R', p, Q and W have meanings as defined herein above, and Pg represents a protecting group such as t-butoxycarbonyl.

Compounds of formula (Ia) in which R$_1$, R$_2$, R$_3$, R and R' have meanings as defined herein, and X' represents —O—(CH$_2$)$_p$-Q-W wherein p, Q and W have meanings as defined herein, may be obtained from compounds of formula (7) by removal of the protecting group using methods described herein or modifications thereof, or using methods well known in the art, e.g., when Pg is t-butoxycarbonyl the protecting group may be removed by treatment with anhydrous acid such as trifluoroacetic acid or hydrochloric acid (HCl) in an organic solvent such as diethyl ether, DCM or EtOAc. The deprotection may be carried out without a solvent when trifluoroacetic acid is used as the reagent.

Alternatively, compounds of formula (Ia) in which X' is —O—(CH$_2$)$_p$-Q-W wherein p, Q and W have meanings as defined herein, may be obtained from sulfonic acid analogs of formula (1) in which X' is hydroxy, and R and R' have meanings as defined herein, by converting a compound of formula (1) to its dialkalimetal salt, e.g., a disodium salt, using aqueous base, e.g., aqueous sodium hydroxide (NaOH), in a polar solvent such as 1,4-dioxane, followed by treatment with an alkylating agent of formula (6) wherein p, Q and W have meanings as defined herein and Lg represents a leaving group such as iodide, bromide, chloride, methanesulfonate or trifluoromethanesulfonate in a polar solvent such as DMF or THF to form compounds of the formula

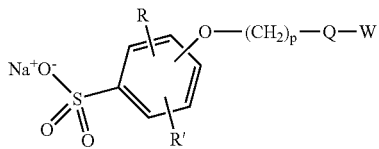

(8)

wherein R, R', p, Q and W have meaning as defined herein.

Compounds of formula (8) wherein R, R', p, Q and W have meaning as defined herein may then be treated with a chlorinating agent such as thionyl chloride or oxalyl chloride to afford sulfonyl chlorides of the formula

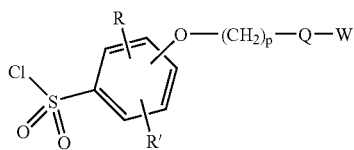

(9)

wherein R, R', p, Q and W have meaning as defined herein. Sulfonyl chlorides of formula (9) can be reacted with amines of formula (3), in which R$_1$, R$_2$ and R$_3$ have meanings as defined herein, in the presence of a base such as TEA, DIEA, NMM or pyridine in an inert solvent such as DCM, DMF or THF to form compounds of formula (Ia) in which X' is —O—(CH$_2$)$_p$-Q-W wherein p, Q and W have meanings defined herein.

Similarly, compounds of formula (Ia) wherein R$_1$, R$_2$, R$_3$, R and R' have meanings as defined herein above, and X' is —S—(CH$_2$)$_p$-Q-W in which p, Q and W have meanings defined herein, may be prepared, e.g., starting from thiols of the formula

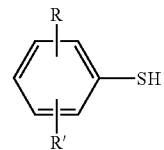

(10)

wherein R and R' have meanings as defined herein. Accordingly, thiols of formula (10) may first be dimerized using methods well known in the art to form disulfides of the formula

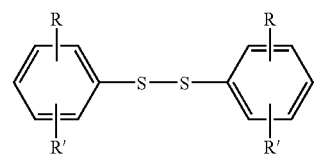

(11)

wherein R and R' have meanings as defined herein.

Compounds of formula (11) wherein R and R' have meanings as defined herein can then be converted to bis sulfonylchloride analogs of the formula

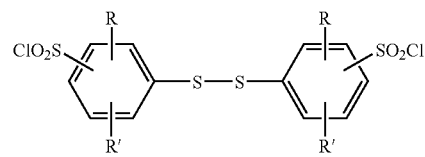

(12)

wherein R and R' have meanings as defined herein, by treatment with chlorosulfonic acid in an inert solvent such as DCM followed by basic hydrolysis using, e.g., aqueous NaOH. The resulting bis sodium salts can then be treated with a chlorinating agent such as thionyl chloride or oxalyl chloride to form sulfonyl chlorides of formula (12).

Sulfonyl chlorides of formula (12) wherein R and R' have meanings as defined herein may be reacted with amines of formula (3) wherein R$_1$, R$_2$ and R$_3$ have meanings as defined herein, in the presence of a base such as TEA, DIEA or NMM in an inert solvent such as DCM, DMF or THF to afford disulfides of the formula

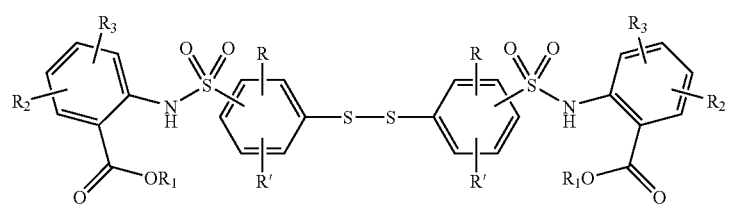

(13)

wherein $R_1$, $R_2$, $R_3$, R and R' have meanings as defined herein above.

Disulfides of formula (13) wherein $R_1$, $R_2$, $R_3$, R and R' have meanings as defined herein can be reduced to afford thiols of the formula

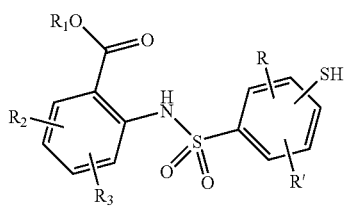

(14)

wherein $R_1$, $R_2$, $R_3$, R and R' have meanings as defined herein above, by treatment with a reducing agent such as sodium borohydride or triphenylphosphine in a polar solvent such as ethanol or THF, respectively.

Alternatively, thiols of formula (14) wherein $R_1$, $R_2$, $R_3$, R and R' have meanings as defined herein may be obtained from phenols of formula (5) wherein $R_1$, $R_2$, $R_3$, R and R' have meanings as defined herein, and Pg represents a protecting group such as t-butoxycarbonyl, by treatment of the latter with dimethylthiocarbamoyl chloride in the presence of a base such as potassium or cesium carbonate in an organic solvent such as DMF or NMP. The resulting thiocarbamate intermediate may then be rearranged by heating at an elevated temperature, e.g., 200° C., to afford compounds of the formula

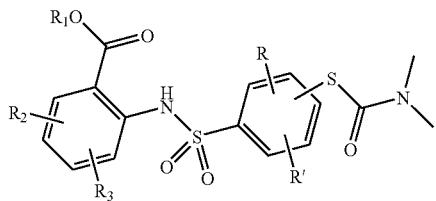

(15)

wherein $R_1$, $R_2$, $R_3$, R and R' have meanings as defined herein above and in which the protecting group has been removed in situ. Compounds of formula (15) provide thiols of formula (14) in which $R_1$ is hydroxy, and $R_2$, $R_3$, R and R' have meanings as defined herein when heated under an inert atmosphere in the presence of a strong base, e.g., potassium hydroxide, in a polar organic solvent such as ethylene glycol.

Thiols of formula (14) wherein $R_1$, $R_2$, $R_3$, R and R' have meanings as defined herein may then be treated with an alkylating agent of formula (6) wherein p, Q and W have meanings as defined herein and Lg represents a leaving group such as iodide, bromide, chloride, methanesulfonate or trifluoromethanesulfonate, in the presence of a base such as potassium or cesium carbonate in an inert solvent such as DMF or THF to form compounds of formula (Ia) wherein X' is —S—$(CH_2)_p$-Q-W in which p, Q and W have meanings as defined herein.

Preferably, the alkylating agent of formula (6) is selected from a group wherein p is an integer of 2 or 3, Q is O or S, Lg is chloride or bromide, and W is

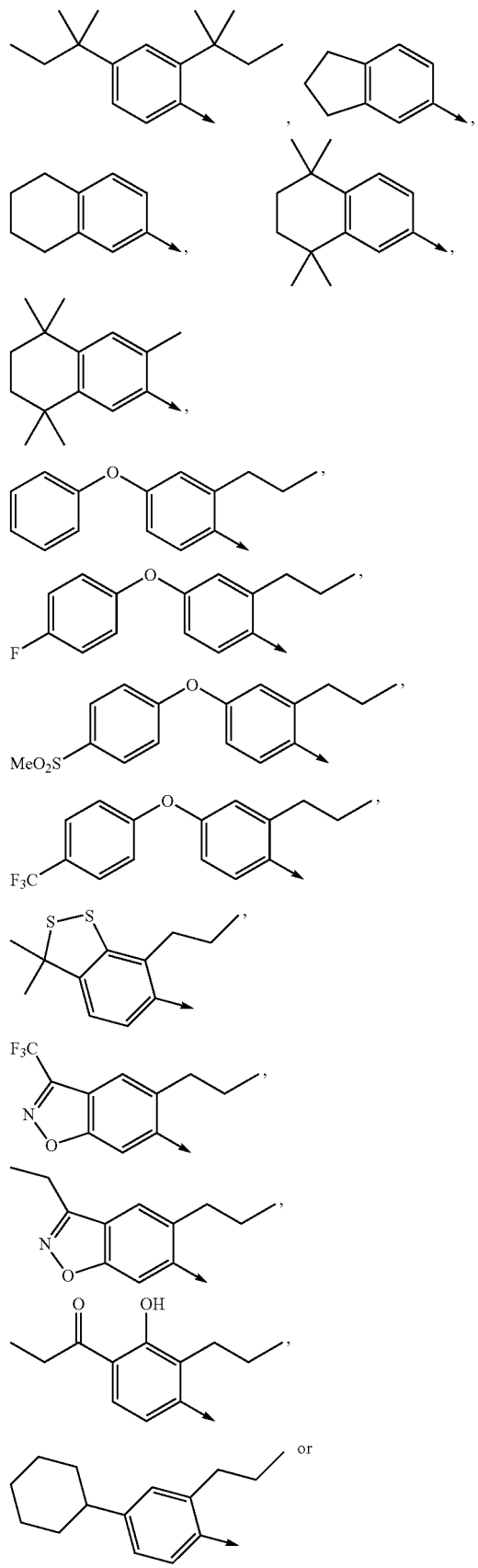

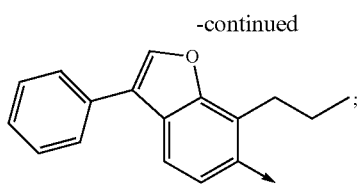
or the alkylating agent of formula (6) is selected from a group wherein p is an integer of 1 or 2, Q is a bond, Lg is chloride, and W is
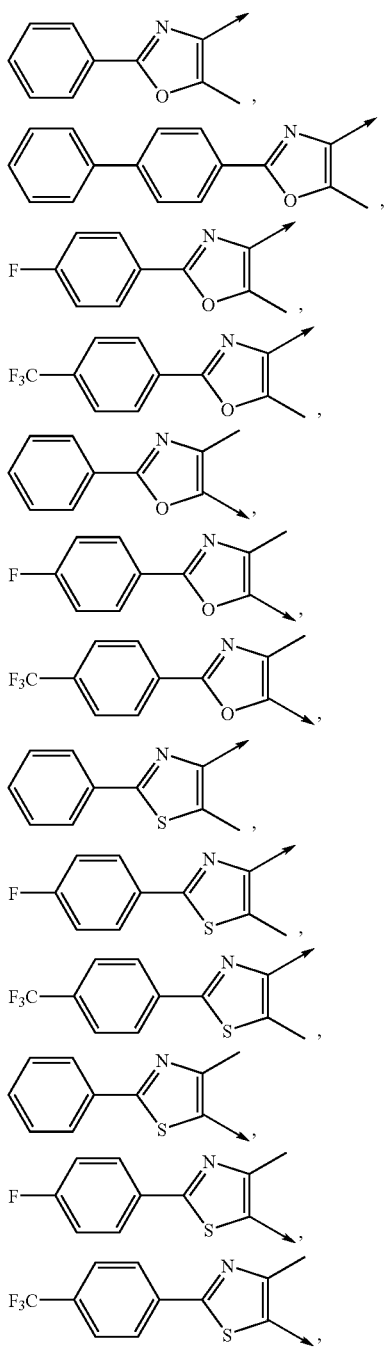
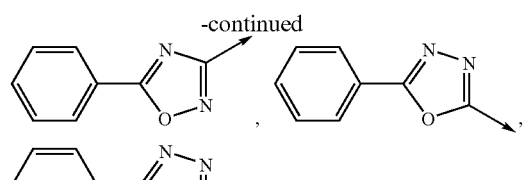
or the alkylating agent of formula (6) is selected from a group wherein p is an integer of 1 or 2, is a bond, Lg is chloride or bromide, and W is
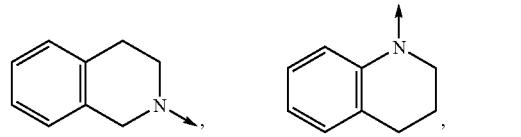

-continued

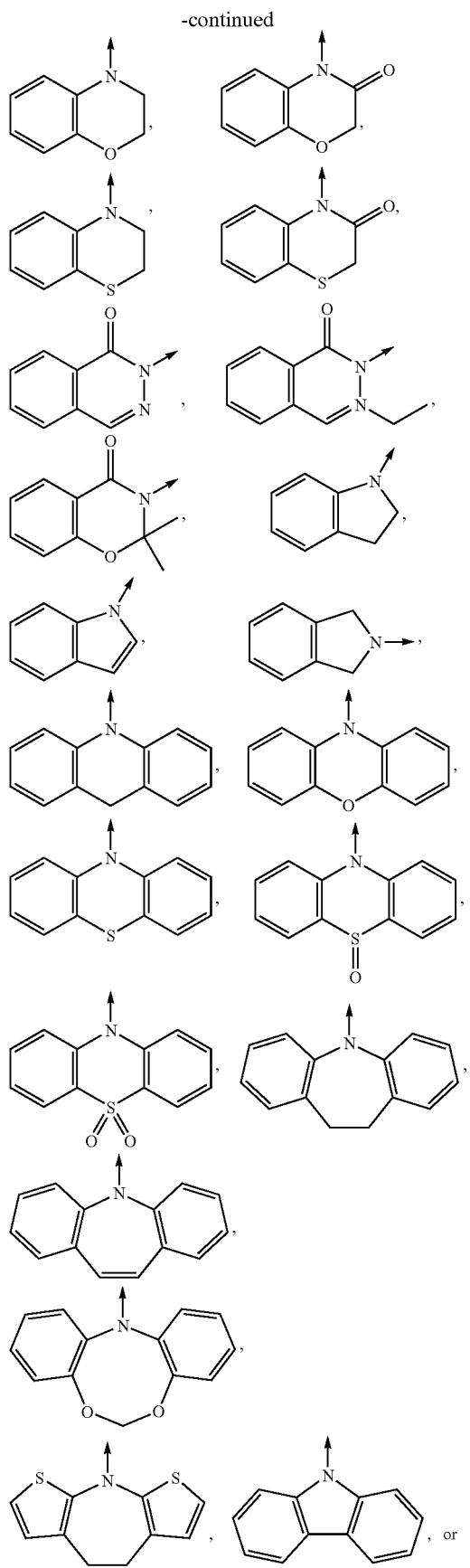

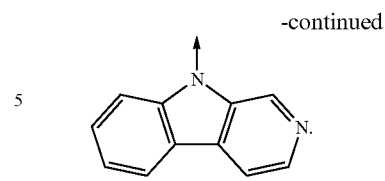

The alkylating agents of formula (6) may be prepared using methods described herein, or modifications thereof, or using methods known in the art, e.g., 4-chloromethyl-5-methyl-2-phenyloxazole and 4-chloromethyl-5-methyl-2-[4-(trifluoromethyl)-phenyl]-oxazole may be prepared using methods described in International PCT Patent Application No. WO 00/64888 or according to *J. Med. Chem.*, Vol. 43, pp. 995-1010 (2000). 1-(3-Bromopropoxy)-4-phenoxy-2-propylbenzene may be prepared as described in International PCT Patent Application No. WO 00/78312.

Preferably, alkylating agents of formula (6) having the formula

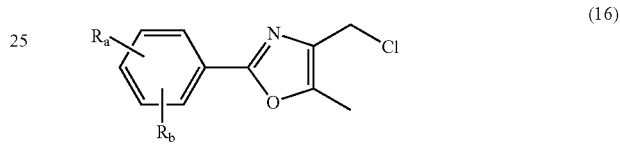

(16)

wherein $R_a$ and $R_b$ are independently hydrogen, halogen, alkyl, alkoxy, trifluoromethyl or aryl, may be prepared by treating a compound of the formula

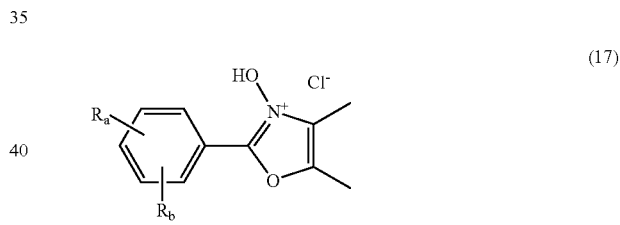

(17)

wherein $R_a$ and $R_b$ have meanings as defined for formula (16), with a chlorinating agent, such as phosphorus oxychloride ($POCl_3$), in acetonitrile. It is essential that the reaction is carried out in acetonitrile in order to obtain alkylating agents of formula (16) in high chemical yield and purity, i.e., the alkylating agents of formula (16) are obtained in high regioselectivity, preferably in greater than 99% selectivity. The chlorination is preferably conducted at an ambient temperature, more preferably at room temperature (RT).

Compounds of formula (17) may be prepared by condensing an aldehyde of the formula

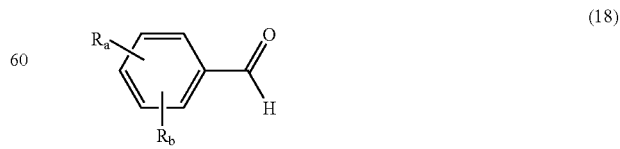

(18)

wherein $R_a$ and $R_b$ have meanings as defined for formula (16), with 2,3-butadione monooxime of the formula

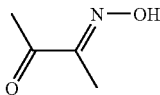

(19)

in the presence of an acid catalyst such as gaseous HCl and an organic solvent, such as EtOAc or acetic acid, preferably glacial acetic acid, to afford compounds of formula (17) wherein $R_a$ and $R_b$ have meanings as defined herein above.

In a preferred embodiment, the alkylating agent of formula (16) is 4-chloromethyl-5-methyl-2[4-(trifluoromethyl)phenyl]-oxazole.

Alternatively, phenols of formula (5) and thiols of formula (14) may also be reacted with alcohols of the formula

HO—(CH$_2$)$_p$-Q-W  (20)

wherein p, Q and W have meanings defined herein, under Mitsunobu conditions, e.g., in the presence of triphenylphoshine and diethyl azodicarboxylate in an organic solvent such as THF, to afford compounds of formula (Ia) in which X' is —O—(CH$_2$)$_p$-Q-W or —S—(CH$_2$)$_r$-Q-W, respectively, and p, Q and W have meanings as defined herein. Alcohols of formula (20) may be prepared by methods described herein or modifications thereof, or by methods well known in the art.

Compounds of formula (Ia) wherein X' is —(CH$_2$)$_p$-Q-W, and p and W have meanings as defined herein and Q represents O or S, may be obtained by reacting compounds of the formula

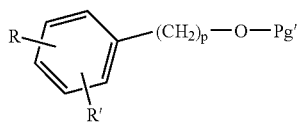

(21)

wherein R, R' and p have meanings as defined herein above, and Pg' represents a protecting group such acyl, e.g. acetyl, or lower alkoxycarbonyl, with chlorosulfonic acid in an inert solvent such as DCM followed by subsequent treatment with a chlorinating agent such as thionyl chloride or oxalyl chloride to afford sulfonyl chlorides of the formula

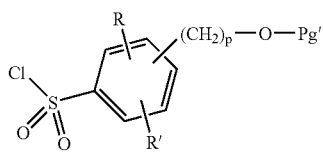

(22)

wherein R, R', p and Pg' have meanings as defined herein above.

Sulfonyl chlorides of formula (22) may be coupled with amines of formula (3) wherein $R_1$, $R_2$ and $R_3$ have meanings as defined herein to afford compounds of the formula

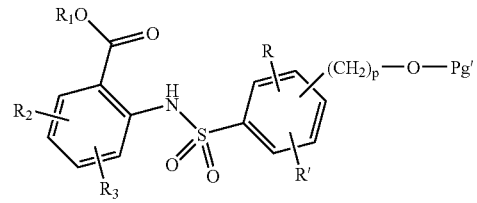

(23)

wherein $R_1$, $R_2$, $R_3$, R, R', p and Pg' have meanings as defined herein under reaction conditions described herein earlier. Subsequent removal of the protecting group using base, e.g., aqueous NaOH in a polar solvent such as methanol, THF or 1,4-dioxane, in particular when Pg' is acetyl, affords alcohols of the formula

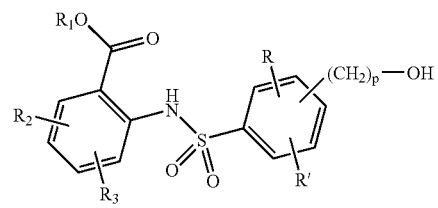

(24)

wherein $R_1$, $R_2$, $R_3$, R, R' and p have meanings as defined herein.

Alcohols of formula (24) may be coupled with phenols of formula W—OH or thiols of formula W—SH, e.g., under Mitsunobu conditions, to form compounds of formula (Ia) wherein $R_1$, $R_2$, $R_3$, R and R' have meanings as defined herein, and X' represents —(CH$_2$)$_p$-Q-W in which p and W have meanings as defined herein, and Q is O or S, respectively.

Alternatively, alcohols of formula (24) may be converted to compounds of the formula

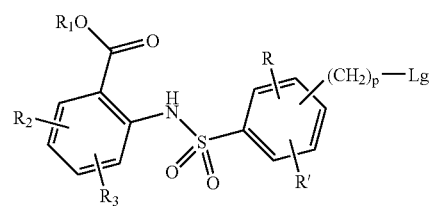

(25)

wherein $R_1$, $R_2$, $R_3$, R and R' have meanings as defined herein and Lg represents a leaving group such as chloride, bromide, iodide, methanesulfonate or trifluoromethanesulfonate, using methods described herein or modifications thereof, or using methods well known in the art. Subsequent reaction of compounds of formula (25) with phenols of formula W—OH or thiols of formula W—SH in the presence of a base such as potassium or cesium carbonate in an inert solvent such as DMF or THF affords compounds of formula (Ia) wherein $R_1$, $R_2$, $R_3$, R and R' have meanings as defined herein, and X' represents —(CH$_2$)$_p$-Q-W in which p and W have meanings as defined herein, and Q is O or S, respectively.

Compounds of formula (Ia) wherein $R_1$, $R_2$, $R_3$, R and R' have meanings as defined herein, and X' represents —C(O)

NR$_4$—(CH$_2$)$_p$-Q-W in which R$_4$, p, Q and W have meanings defined herein, may be prepared by reacting an activated derivative of a carboxylic acid of the formula

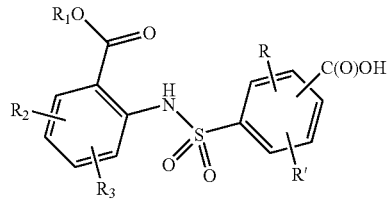
(26)

wherein R$_2$, R$_3$, R and R' have meanings as defined herein and R$_1$ is optionally substituted alkyl, aryl, heteroaryl, aralkyl or cycloalkyl, with amines, or acid addition salts thereof, of the formula

R$_4$—NH—(CH$_2$)$_p$-Q-W (27)

wherein R$_4$, p, Q and W have meanings as defined herein. Carboxylic acids of formula (26) and amines of formula (27) may be prepared using methods described herein or modifications thereof, or using methods known in the art.

Similarly, compounds of formula (Ia) wherein R$_1$, R$_2$, R$_3$, R and R' have meanings as defined herein, and X' represents —Z—(CH$_2$)$_p$—C(O)NR$_5$—W in which Z, p, R$_5$ and W have meanings as defined herein, may be prepared by reacting an activated derivative of a carboxylic acid of the formula

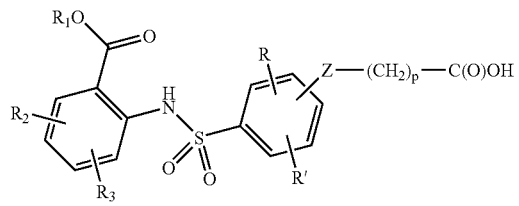
(28)

wherein R$_2$, R$_3$, R, R', Z and p have meanings as defined herein and R$_1$ is optionally substituted alkyl, aryl, heteroaryl, aralkyl or cycloalkyl, with amines, or acid addition salts thereof, of the formula

R$_5$—NH—W (29)

wherein R$_5$ and W have meanings as defined herein. Carboxylic acids of formula (28) and amines of formula (29) may be prepared using methods described herein or modifications thereof, or using methods known in the art.

In the processes cited herein, activated derivatives of carboxylic acids, e.g., those derived from carboxylic acids of formula (26) and (28), include acid chlorides, bromides and fluorides, mixed anhydrides, lower alkyl esters, and activated esters thereof, and adducts formed with coupling agents such as 1-ethyl-3-(3-dimethylaminopropyl)carbodiimide hydrochloride (EDCI), O-(1,2-dihydro-2-oxo-1-pyridyl)-N,N,N', N'-tetramethyluronium tetrafluoroborate and the like. Mixed anhydrides are preferably such from pivalic acid, or lower alkyl hemiesters of carbonic acids, such as ethyl or isobutyl analogs. Activated esters include, for example, succinimido, phthalimido or 4-nitrophenyl esters. The reaction of an activated derivative of a carboxylic acid, e.g., those derived from carboxylic acids of formula (26) or (28), with an amine, e.g., those of formula (27) or (29), respectively, may be carried out in the presence of a base such as TEA, DIEA or NMM in an inert solvent such as DCM, DMF or THF. Carboxylic acids of formula (26) and (28) can be converted to their activated derivatives using methods described herein or in the art.

Compounds of formula (Ia) wherein R$_1$, R$_2$, R$_3$, R and R' have meanings as defined herein, and X' represents —Z—(CH$_2$)$_p$NR$_6$C(O)—W, —Z—(CH$_2$)$_p$—NR$_6$C(O)NH—W or —Z—(CH$_2$)$_p$—NR$_6$C(O)O—W in which Z, p, R$_6$ and W have meanings as defined herein, may be obtained by reacting amines of the formula

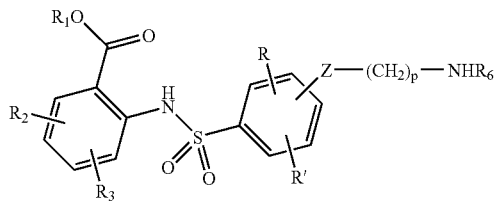
(30)

wherein R$_2$, R$_3$, R, R', Z, p and R$_6$ have meanings as defined herein, and R$_1$ is optionally substituted alkyl, aryl, heteroaryl, aralkyl or cycloalkyl, with a N-derivatizing agent such as an activated carboxylic acid derivative, an isocyanate or a chloroformate, respectively, in the presence of a base such as TEA, DIEA or NMM in an inert solvent such as DCM, DMF or THF. Amines of formula (30) may be prepared using methods described herein or modifications thereof, or using methods known in the art.

Similarly, compounds of formula (Ia) wherein R$_1$, R$_2$, R$_3$, R and R' have meanings as defined herein, and X' represents —NHC(O)—(CH$_2$)$_p$-Q-W, and p, Q and W have meanings as defined herein, may be obtained by treatment of amines of the formula

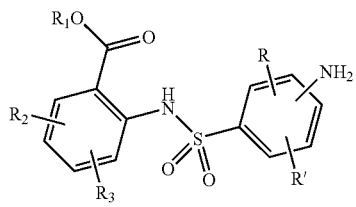
(31)

wherein R$_2$, R$_3$, R and R' have meanings as defined herein, and R$_1$ is optionally substituted alkyl, aryl, heteroaryl, aralkyl or cycloalkyl with an activated derivative of a carboxylic acid of the formula

HOOC—(CH$_2$)$_p$-Q-W (32)

wherein p, Q and W have meanings as defined herein, following protocol described herein above. Amines of formula (31) and carboxylic acids of formula (32) may be prepared using methods described herein or modifications thereof, or using methods known in the art.

Compounds of formula (I) wherein A-B represents —Y—C(R$_8$)$_2$ in which Y and R$_8$ have meanings as defined herein may be prepared by reacting compounds of the formula

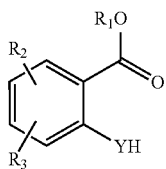
(33)

wherein R$_1$, R$_2$, R$_3$ and Y have meanings as defined herein, with an alkylating agent of the formula

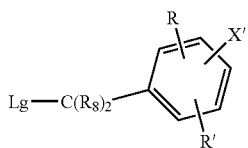
(34)

wherein R and R' have meanings as defined herein, Lg represents a leaving group such as chloride, bromide, iodide, methanesulfonate or trifluoromethanesulfonate, and X' represents X as defined herein, or X' is a group convertible to X, in the presence of a base such as potassium carbonate, cesium carbonate or sodium hydride in an inert solvent such as DMF or THF to afford compounds of the formula

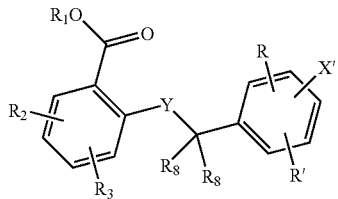
(Ib)

wherein R$_1$, R$_2$, R$_3$, R$_8$, R, R', Y and X' have meanings as defined herein. Alkylating agents of formula (34) may be obtained using methods described herein in the illustrative Examples, or modifications thereof, or using methods known in the art.

Preferably, the alkylating agents of formula (34) have the formula

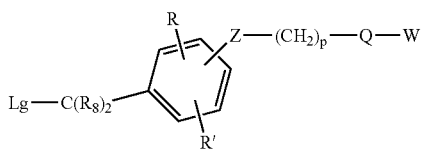
(35)

wherein R, R$_1$ and R$_7$ are hydrogen, Z is O or S, p is an integer of 1 or 2, Q is a bond, Lg is bromide, and W is

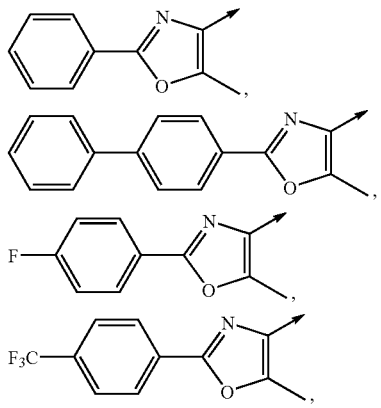

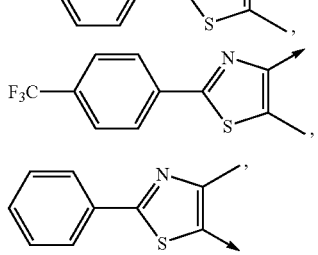

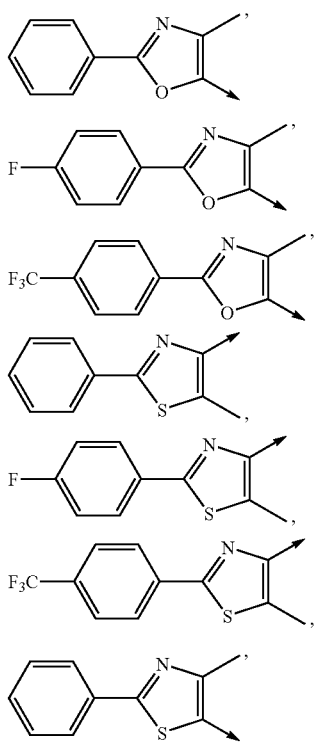

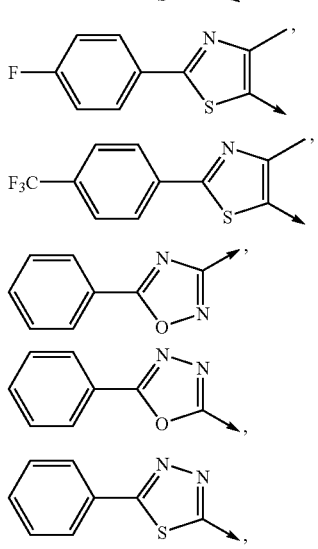

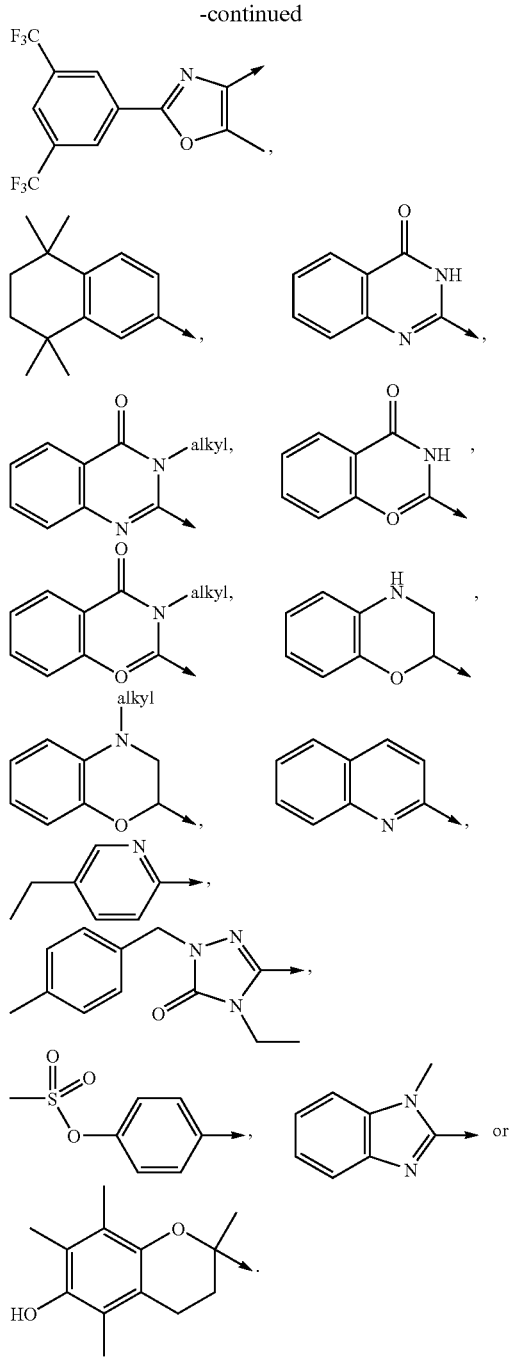

Alternatively, compounds of formula (Ib) wherein X' represents X as defined herein may be obtained from compounds of formula (Ib) wherein X' is a group convertible to X using methods described herein for compounds of formula (Ia), or modifications thereof, or using methods well known in the art.

Compounds of formula (Ia) and (Ib) in which $R_1$ is optionally substituted alkyl, aryl, heteroaryl, aralkyl or cycloalkyl can be converted to corresponding compounds of formula (Ia) and (Ib) in which $R_1$ is hydrogen using reaction conditions described herein, or modifications thereof, or using methods know in the art, e.g., compounds of formula (Ia) and (Ib) in which $R_1$ is lower alkyl such as methyl or ethyl may be treated with an aqueous base such as sodium or potassium hydroxide in a polar solvent such as methanol, ethanol, 1,4-dioxane or THF to afford compounds of formula (Ia) and (Ib) in which $R_1$ is hydrogen.

The starting compounds and intermediates which are converted to the compounds of the invention in a manner described herein, functional groups present, such as amino, thiol, carboxyl, and hydroxy groups, are optionally protected by conventional protecting groups that are common in preparative organic chemistry. Protected amino, thiol, carboxyl, and hydroxy groups are those that can be converted under mild conditions into free amino, thiol, carboxyl and hydroxy groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxy group, amino group, etc.), the structure and stability of the molecule of which the substituent is a part and the reaction conditions.

Well-known protecting groups that meet these conditions and their introduction and removal are described, e.g., in McOmie, "*Protective Groups in Organic Chemistry*", Plenum Press, London, N.Y. (1973); and Greene and Wuts, "*Protective Groups in Organic Synthesis*", John Wiley and Sons, Inc., NY (1999).

The above-mentioned reactions are carried out according to standard methods, in the presence or absence of diluent, preferably such as are inert to the reagents and are solvents thereof, of catalysts, condensing or said other agents respectively and/or inert atmospheres, at low temperatures, RT or elevated temperatures (preferably at or near the boiling point of the solvents used), and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

The invention also relates to any novel starting materials and processes for their manufacture.

Depending on the choice of starting materials and methods, the compounds may be in the form of one of the possible isomers or mixtures thereof, for example, as substantially pure geometric (cis or trans) isomers, optical isomers (antipodes), racemates, or mixtures thereof. The aforesaid possible isomers or mixtures thereof are within the purview of this invention.

Any resulting mixtures of isomers can be separated on the basis of the physico-chemical differences of the constituents, into the pure geometric or optical isomers, diastereoisomers, racemates, for example by chromatography and/or fractional crystallization.

Any resulting racemates of final products or intermediates can be resolved into the optical antipodes by known methods, e.g., by separation of the diastereoisomeric salts thereof, obtained with an optically active acid or base, and liberating the optically active acidic or basic compound. Carboxylic acid derivatives can thus be resolved into their optical antipodes, e.g., by fractional crystallizaton of D- or L-(alpha-methylbenzylamine, cinchonidine, cinchonine, quinine, quinidine, ephedrine, dehydroabietylamine, brucine or strychnine)-salts. Racemic products can also be resolved by chiral chromatography, e.g., high pressure liquid chromatography using a chiral adsorbent.

Finally, compounds of the invention are either obtained in the free form, or as a salt thereof if salt forming groups are present.

Acidic compounds of the invention may be converted into salts with pharmaceutically acceptable bases, e.g. an aqueous alkali metal hydroxide, advantageously in the presence of an ethereal or alcoholic solvent, such as a lower alkanol. From the solutions of the latter, the salts may be precipitated with ethers, e.g. diethyl ether. Resulting salts may be converted into the free compounds by treatment with acids. These or other salts can also be used for purification of the compounds obtained.

Compounds of the invention having basic groups can be converted into acid addition salts, especially pharmaceutically acceptable salts. These are formed, for example, with inorganic acids, such as mineral acids, for example sulfuric acid, a phosphoric or hydrohalic acid, or with organic carboxylic acids, such as ($C_1$-$C_4$)-alkanecarboxylic acids which, for example, are unsubstituted or substituted by halogen, for example acetic acid, such as saturated or unsaturated dicarboxylic acids, for example oxalic, succinic, maleic or fumaric acid, such as hydroxy-carboxylic acids, for example glycolic, lactic, malic, tartaric or citric acid, such as amino acids, for example aspartic or glutamic acid, or with organic sulfonic acids, such as ($C_1$-$C_4$)-alkyl-sulfonic acids (for example methanesulfonic acid) or arylsulfonic acids which are unsubstituted or substituted (for example by halogen). Preferred are salts formed with hydrochloric acid, methanesulfonic acid and maleic acid.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

As described herein above, the compounds of the present invention bind to PPARs, and thus may be employed for the treatment of conditions mediated by the PPARs. Such compounds may therefore be employed therapeutically for the treatment of dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, IBDs, ulcerative colitis, Crohn's disease, and conditions in which impaired glucose tolerance, hyperglycemia and insulin resistance are implicated, such as type-1 and type-2 diabetes, and Syndrome X.

The present invention further provides pharmaceutical compositions comprising a therapeutically effective amount of a pharmacologically active compound of the instant invention, alone or in combination with one or more pharmaceutically acceptable carriers.

The pharmaceutical compositions according to the invention are those suitable for enteral, such as oral or rectal; transdermal and parenteral administration to mammals, including man, for the treatment of conditions mediated by PPAR receptors, in particular, PPARα and PPARγ. Such conditions include dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, IBDs, ulcerative colitis and Crohn's disease, and conditions in which impaired glucose tolerance, hyperglycemia and insulin resistance are implicated, such as type-1 and type-2 diabetes, and Syndrome X. Thus, the pharmacologically active compounds of the invention may be employed in the manufacture of pharmaceutical compositions comprising an effective amount thereof in conjunction or admixture with excipients or carriers suitable for either enteral or parenteral application. Preferred are tablets and gelatin capsules comprising the active ingredient together with:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbants, colorants, flavors and sweeteners. Injectable compositions are preferably aqueous isotonic solutions or suspensions, and suppositories are advantageously prepared from fatty emulsions or suspensions.

Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Accordingly, the present invention provides pharmaceutical compositions as described above for the treatment of conditions mediated by PPARs, preferably, dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, IBDs, ulcerative colitis, Crohn's disease, and conditions in which impaired glucose tolerance, hyperglycemia and insulin resistance are implicated, such as type-1 and type-2 diabetes, and Syndrome X.

The pharmaceutical compositions may contain a therapeutically effective amount of a compound of the invention as defined above, either alone or in a combination with another therapeutic agent, e.g., each at an effective therapeutic dose as reported in the art. Such therapeutic agents include:

a) antidiabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; protein tyrosine phosphatase-1B (PTP-1B) inhibitors such as PTP-112; GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose cotransporter inhibitors such as T-1095; glycogen phosphorylase A inhibitors such as BAY R3401; biguanides such as mefformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as LAF237;

b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid and aspirin;

c) ant-obesity agents such as orlistat; and d) ant-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as aliskiren; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.

Other specific anti-diabetic compounds are described by Patel Mona in *Expert Opin Investig Drugs*, 2003, 12(4), 623-633, in the FIGS. 1 to 7, which are herein incorporated by reference. A compound of the present invention may be administered either simultaneously, before or after the other active ingredient, either separately by the same or different route of administration or together in the same pharmaceutical formulation.

The structure of the therapeutic agents identified by code numbers, generic or trade names may be taken from the actual edition of the standard compendium "The Merck Index" or from databases, e.g., Patents International (e.g. IMS World Publications). The corresponding content thereof is hereby incorporated by reference.

Accordingly, the present invention provides pharmaceutical compositions comprising a therapeutically effective amount of a compound of the invention in combination with a therapeutically effective amount of another therapeutic agent, preferably selected from anti-diabetics, hypolipidemic agents, anti-obesity agents or anti-hypertensive agents, most preferably from antidiabetics or hypolipidemic agents as described above.

The present invention further relates to pharmaceutical compositions as described above for use as a medicament.

The present invention further relates to use of pharmaceutical compositions or combinations as described above for the preparation of a medicament for the treatment of conditions mediated by PPARs, preferably, dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, IBDs, ulcerative colitis, Crohn's disease, and conditions in which impaired glucose tolerance, hyperglycemia and insulin resistance are implicated, such as type-1 and type-2 diabetes, and Syndrome X.

Thus, the present invention also relates to a compound of formula (I) for use as a medicament; to the use of a compound of formula (I) for the preparation of a pharmaceutical composition for the prevention and/or treatment of conditions mediated by PPARs, and to a pharmaceutical composition for use in conditions mediated by PPARs comprising a compound of formula (I), or a pharmaceutically acceptable salt thereof, in association with a pharmaceutically acceptable diluent or carrier therefore.

The present invention further provides a method for the prevention and/or treatment of conditions mediated by PPARs, which comprises administering a therapeutically effective amount of a compound of the present invention.

A unit dosage for a mammal of about 50-70 kg may contain between about 1 mg and 1000 mg, advantageously between about 5-500 mg of the active ingredient. The therapeutically effective dosage of active compound is dependent on the species of warm-blooded animal (mammal), the body weight, age and individual condition, on the form of administration, and on the compound involved.

In accordance with the foregoing the present invention also provides a therapeutic combination, e.g., a kit, kit of parts, e.g., for use in any method as defined herein, comprising a compound of formula (I), or a pharmaceutically acceptable salt thereof, to be used concomitantly or in sequence with at least one pharmaceutical composition comprising at least another therapeutic agent, preferably selected from anti-diabetic agents, hypolipidemic agents, anti-obesity agents or anti-hypertensive agents. The kit may comprise instructions for its administration.

Similarly, the present invention provides a kit of parts comprising: (i) a pharmaceutical composition of the invention; and (ii) a pharmaceutical composition comprising a compound selected from an anti-diabetic, a hypolipidemic agent, an anti-obesity agent, an anti-hypertensive agent, or a pharmaceutically acceptable salt thereof, in the form of two separate units of the components (i) to (ii).

Likewise, the present invention provides a method as defined above comprising co-administration, e.g., concomitantly or in sequence, of a therapeutically effective amount of a compound of formula (I), or a pharmaceutically acceptable salt thereof, and a second drug substance, said second drug substance being an anti-diabetic, a hypolipidemic agent, an anti-obesity agent or an anti-hypertensive agent, e.g., as indicated above.

Preferably, a compound of the invention is administered to a mammal in need thereof.

Preferably, a compound of the invention is used for the treatment of a disease which responds to modulation of the PPAR activity.

Preferably, the condition associated with PPAR activity is selected from dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, IBDs, ulcerative colitis, Crohn's disease, and conditions in which impaired glucose tolerance, hyperglycemia and insulin resistance are implicated, such as type-1 and type-2 diabetes, and Syndrome X.

Finally, the present invention provides a method or use which comprises administering a compound of formula (I) in combination with a therapeutically effective amount of an anti-diabetic agent, a hypolipidemic agent, an anti-obesity agent or an anti-hypertensive agent.

Ultimately, the present invention provides a method or use which comprises administering a compound of formula (I) in the form of a pharmaceutical composition as described herein.

As used throughout the specification and in the claims, the term "treatment" embraces all the different forms or modes of treatment as known to those of the pertinent art and in particular includes preventive, curative, delay of progression and palliative treatment.

The above-cited properties are demonstrable in vitro and in vivo tests, using advantageously mammals, e.g. mice, rats, dogs, monkeys or isolated organs, tissues and preparations thereof. Said compounds can be applied in vitro in the form of solutions, e.g. preferably aqueous solutions, and in vivo either enterally, parenterally, advantageously intravenously, e.g. as a suspension or in aqueous solution. The dosage in vitro may range between about $10^{-3}$ molar and $10^{-10}$ molar concentrations. A therapeutically effective amount in vivo may range depending on the route of administration, between about 1 and 500 mg/kg, preferably between about 5 and 100 mg/kg.

The activity of a compound according to the invention can be assessed by the following methods or methods well described in the art:

The in vitro functional binding to the PPARα, PPARδ and PPARγ receptors is determined as follows:

The functional binding assays for the PPARα, PPARδ and PPARγ receptors are a variation of the coactivator-dependent receptor ligand assay (CARLA) (Krey et al., *Molecular Endocrinology* 1997, 11, 779-791). The present CARLA assays use a TR-FRET detection method previously reviewed (Hemmila, *J. Biomol. Screening* 1999, 4, 303-307; Mathis, *J. Biomol. Screening* 1999, 4, 309-313). All assays included 3 nM of the glutathione-S-transferase (GST) fusion proteins of either the hPPARα ligand binding domain (LBD) (amino acids 167-468) (GST-hPPARα LBD), GST-hPPARδ LBD (amino acids 139-442) or GST-hPPARγ LBD (amino acids 175-476); 3 nM Eu-labelled anti-GST antibody (Wallac); 30 nM biotinylated steroid receptor coactivator-1 (SRC-1) peptide (an N-terminal biotinylated peptide, CPSSHSSLTERH-KILHRLLQEGSPS, derived from amino acids 676-700 of SRC-1); and 10 nM streptavidin-labelled allophycocyanin (APC; Prozyme). The binding of a ligand to a PPAR LBD alters the conformation of the LBD and permits the biotinylated SRC-1 peptide to bind. This brings the Eu-labelled anti-GST antibody and the strepavidin-labelled APC in close proximity, thereby facilitating fluorescence energy transfer. The biotinylated SRC-1 peptide is prepared by standard solid-phase peptide synthetic methods. The GST-PPAR LBDs are expressed in pGEX vectors (Amersham Pharmacia) in the *E. coli* strain BL21 (DE3) using standard expression conditions at 18° C. In some cases the GST-PPAR LBDs are co-expressed with groESL. The GST fusion proteins are purified on glutathione sepharose affinity columns (Amersham Pharmacia) using the method described by the manufacturer. The assay buffer contained 50 mM Tris pH 7.4, 50 mM KCl, 0.1% BSA, and 1 mM DTT. The assay is carried out in black half area 96-well plates in a final volume of 25 μl. After mixing all components, the reaction mixture stands for 3 h at RT before reading the TR-FRET signal on a Wallac Victor 2 plate reader (measuring the ratio of signals at 665 nm and 620 nm). $EC_{50}$ values are estimated with the Excel add-in program XLFit (ID Business Solutions, Guildford, Surrey, UK) utilizing a 4-parameter logistic equation.

The glucose and insulin lowering activity in vivo can be evaluated as follows:

Adult male C57BL ob/ob mice (Jackson Lab, Bar Harbor, Me.) at the age of 11 weeks are housed six per cage in a reversed light cycle room (light on from 6:00 p.m. to 6:00 a.m.) and given access to Purina rodent chow and water ad libitum. On day 1 tail blood samples are taken at 8:00 am and plasma glucose levels are determined. The animals are randomly assigned to the control and compound groups. The means of plasma glucose values of the groups were matched. Animals are then orally dosed with vehicle (0.5% carboxymethyl-cellulose with 0.2% Tween-80) or compounds (at 30 mg/kg) in vehicle. The mice are dosed daily for a total of 3 days. On day 4 basal blood samples are taken. The plasma samples are analyzed for glucose concentrations using a YS12700 Dual Channel Biochemistry Analyzer (Yellow Springs Instrument Co., Yellow Springs, Ohio) and insulin concentrations using an ELISA assay.

Illustrative of the invention, the compound of Example 1 demonstrates an $EC_{50}$ of about 8 nM in the PPARα receptor binding assay, an $EC_{50}$ of about 5 nM in the PPARγ receptor binding assay, and an $EC_{50}$ of about 3500 nM in the PPARδ receptor binding assay Furthermore, said compound significantly lowers serum glucose and insulin levels at a daily dose of about 30 mg/kg p.o. in the ob/ob mice.

The following Examples are intended to illustrate the invention and are not to be construed as being limitations thereon. Temperatures are given in degrees Centigrade. If not mentioned otherwise, all evaporations are performed under reduced pressure, preferably between about 5 and 100 mmHg. The structure of final products, intermediates and starting materials is confirmed by standard analytical methods, e.g. microanalysis, melting point (m.p.) and spectroscopic characteristics (e.g. MS, IR, NMR). Abbreviations used are those conventional in the art.

Example 1

2-Methyl-6-[4-(5-methyl-2-phenyl-oxazol-4-yl-methoxy)-benzenesulfonylamino]-benzoic acid

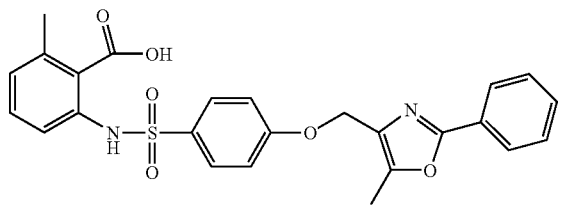

A. 4-Hydroxybenzenesulfonic acid disodium salt

A solution of sodium 4-hydroxybenzenesulfonate dihydrate (15 g, 64.6 mmol) in 64.66 mL of 1 N aqueous NaOH is heated at reflux for 1 h, cooled and concentrated under vacuum. Toluene is added, and the mixture is again concentrated under vacuum. This process of toluene addition followed by concentration under vacuum is repeated twice more to remove water. The resulting white solid is dried in a vacuum oven at 60° C. overnight to give 4-hydroxybenzenesulfonic acid disodium salt.

B. 4-(5-Methyl-2-phenyl-oxazol-4-ylmethoxy)-benzenesulfonic acid sodium salt

A mixture of the title A compound, 4-hydroxybenzenesulfonic acid disodium salt (14.11 g, 64.65 mmol) and 4-chloromethyl-5-methyl-2-phenyl-oxazole (16.11 g, 77.58 mmol) in 55 mL of DMF is heated under nitrogen at 110° C. for 18 h. The cooled reaction mixture is filtered and the solid obtained is washed with 100 mL of DCM. The solid is triturated with an additional 50 mL of DCM, filtered and dried overnight to give 4-(5-methyl-2-phenyl-oxazol-4-yl-methoxy)-benzenesulfonic acid sodium salt as a white powder: ESI-MS 346.05 [M+1]$^+$, 344.02 [M−1]$^−$.

C. 4-(5-Methyl-2-phenyl-oxazol-4-ylmethoxy)-benzenesulfonyl chloride

Thionyl chloride (50 mL) is added to the title B compound, 4-(5-methyl-2-phenyl-oxazol-4-ylmethoxy)-benzenesulfonic acid sodium salt (18.1 g, 52.46 mmol) at 0° C. After 10 min, the ice bath is removed and the mixture is stirred at RT for 30 min. An additional 50 mL of thionyl chloride is added, followed by about 1 mL of DMF. The solid dissolves within 10 min. Stirring is continued for an additional 2.5 h and the mixture is then concentrated under vacuum. The resulting yellow solid is partitioned between 250 mL of water and 250 mL of EtOAc (warm). The organic layer is further washed with water (3×250 mL), 0.1 N aqueous NaOH (4×250 mL) and brine (1×250 mL). The organic phase is dried over anhydrous magnesium sulfate, filtered and concentrated under vacuum to give 4-(5-methyl-2-phenyl-oxazol-4-ylmethoxy)-benzenesulfonyl chloride as a yellow solid: ESI-MS 363.99 [M+1]$^+$.

D. 2-Methyl-6-[4-(5-methyl-2-phenyl-oxazol-4-yl-methoxy)-benzenesulfonylamino]-benzoic acid Sodium bicarbonate (159 mg, 1.89 mmol) and 2-amino-6-methylbenzoic acid (95.5 mg, 0.63 mmol) are dissolved in a mixture of 1 mL of THF and 1.5 mL of water and heated to 60° C. A solution of the title C compound, 4-(5-methyl-2-phenyl-oxazol-4-ylmethoxy)-benzenesulfonyl chloride (200 mg, 0.55 mmol) in 1 mL of THF is then added dropwise. The mixture is heated for an additional 2 h at 60° C., after which most of the THF is removed by passing a stream of nitrogen gas over the solution. The residue is partitioned between EtOAc and 1 N aqueous HCl. The organic phase is dried over anhydrous magnesium sulfate, filtered, and concentrated under vacuum to give crude product which is purified by chromatography on silica gel with an EtOAc (15%)-hexane (85%) mixture (containing 0.5% formic acid) as the eluent to give 2-methyl-6-[4-(5-methyl-2-phenyl-oxazol-4-yl-methoxy)-benzenesulfonylamino]-benzoic acid as a white solid: m.p. 167-170° C.; ESI-MS 479 [M+1]$^+$.

Example 2

4-Chloro-2-{4-[2-(5-methyl-2-phenyl-oxazol-4-yl)-ethoxy]-benzenesulfonylamino}-benzoic acid

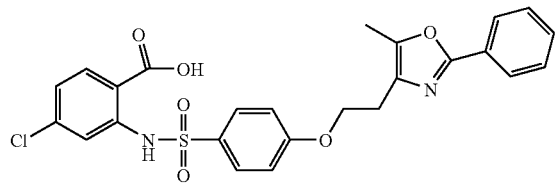

A. 4-Benzyloxybenzenesulfonic acid sodium salt

Aqueous NaOH (40 mL of a 15% aqueous solution, 150 mmol) is added to 20 g (86.2 mmol) of 4-hydroxybenzenesulfonic acid sodium salt dihydrate at RT. An additional 20 mL of water is added, and the mixture is warmed slightly to dissolve the salt. Benzyl bromide (19.2 g, 112.1 mmol) in 8 mL of ethanol is then added in several portions. The mixture is heated to reflux. After 30 min, additional 20 mL of water is added, and heating is continued for 3.5 h, followed by continued stirring at RT overnight. After cooling in the refrigerator for 3 h, the solid product is collected by filtration and washed with water (20 mL), ethanol (40 mL), and ether (40 mL) and then dried overnight under vacuum to give 4-benzyloxybenzenesulfonic acid sodium salt.

B. 4-Benzyloxybenzenesulfonyl chloride

Thionyl chloride (200 mL, 326.2 grams, 2742 mmol) is added to the solid title A compound, 4-benzyloxybenzenesulfonic acid sodium salt, followed by 10 drops of DMF. The mixture is heated to reflux overnight and then concentrated under vacuum. Hot toluene (250 mL) is added, and the mixture is filtered. The filtrate is concentrated under vacuum. Toluene is again added to the residue followed by filtration and concentration under vacuum to give 4-benzyloxybenzenesulfonyl chloride as a white solid.

C. 2-(4-Benzyloxybenzenesulfonylamino)-4-chlorobenzoic acid methyl ester

Methyl 2-amino-4-chlorobenzoate (2.5 g, 13.3 mmol) is added to a solution of 2.5 g (8.84 mmol) of the title B compound, 4-benzyloxybenzenesulfonyl chloride in 50 mL of DCM, then 1.4 g (1.43 mL, 17.68 mmol) of pyridine is added. The mixture is stirred overnight at RT. The organic solution is then washed with water and brine, dried over anhydrous magnesium sulfate, filtered, and concentrated under vacuum to a slightly red solid. The solid is adsorbed on 13 g of silica gel and chromatographed (FlashElute 40M silica gel column) using 1 L of an EtOAc (15%)-hexane (85%) mixture as the eluent, followed by 1 L of DCM to afford 2-(4-benzyloxy-benzene-sulfonylamino)-4-chloro-benzoic acid methyl ester as a white solid.

D. 2-[(4-Benzyloxybenzenesulfonyl)-(t-butoxycarbonyl)amino]-4-chloro-benzoic acid methyl ester TEA (1.45 g, 14.31 mmol) and DMAP (585 mg, 4.77 mmol) are added to a solution of the title C compound, 2-(4-benzyloxybenzenesulfonyl-amino)-4-chloro-benzoic acid methyl ester (2.06 g, 4.77 mmol) in 30 mL of THF at 0° C., followed by di-t-butyl dicarbonate (1.56 g, 7.16 mmol). The ice bath is then removed, and the reaction is stirred overnight at RT. The mixture is concentrated under vacuum, and the product is taken up in EtOAc, and extracted with 0.5 N aqueous HCl. The organic layer is washed with brine, dried over anhydrous magnesium sulfate, and concentrated under vacuum to give 2-[(4-benzyloxy-benzenesulfonyl)-(t-butoxycarbonyl)-amino]-4-chloro-benzoic acid methyl ester.

E. 2-[(4-Hydroxybenzenesulfonyl)-(t-butoxycarbonyl)amino]4-chloro-benzoic acid methyl ester A solution of the title D compound, 2-[(4-benzyloxy-benzenesulfonyl)-(t-butoxycarbonyl)-amino]-4-chloro-benzoic acid methyl ester (2.45 g, 4.61 mmol) in 30 mL of EtOAc containing 1.2 g of 10% palladium on carbon is shaken under 50 psi of hydrogen at RT overnight. The mixture is then filtered and concentrated to give 2-[(4-hydroxybenzene-sulfonyl)-(t-butoxycarbonyl)amino]4-chloro-benzoic acid methyl ester as a white foam.

F. Methanesulfonic acid 2-(5-methyl-2-phenyl-oxazol-4-yl)-ethyl ester

TEA (4.98 g, 49.2 mmol) and methanesulfonyl chloride (3.38 g, 29.5 mmol) is added to a solution of 2-(5-methyl-2-phenyl-oxazol-4-yl)-ethanol (5 g, 24.6 mmol) in 100 mL of DCM at 0° C. The resulting mixture is stirred at RT overnight. The mixture is then washed with water and brine, and the organic solution is dried over anhydrous magnesium sulfate and concentrated to give methanesulfonic acid 2-(5-methyl-2-phenyl-oxazol-4-yl)-ethyl ester as a yellow solid.

G. 4-Chloro-2-{4-[2-(5-methyl-2-phenyl-oxazol-4-yl)-ethoxy]-benzenesulfonyl-(t-butoxycarbonyl) amino}-benzoic acid methyl ester A mixture of the title E compound, 2-[(4-hydroxybenzenesulfonyl)-(t-butoxycarbonyl)-amino]-4-chloro-benzoic acid methyl ester (300 mg, 0.73 mmol), the title F compound, methanesulfonic acid 2-(5-methyl-2-phenyl-oxazol-4-yl)-ethyl ester (246 mg, 0.87 mmol) and cesium carbonate (475 mg, 1.46 mmol) is stirred in DMF at 60° C. overnight. The mixture is cooled and the product is taken up in EtOAc. The solution is washed with brine, dried over anhydrous magnesium sulfate, and concentrated to give the crude product which is purified by flash chromatography on silica gel using an EtOAc (15%)-hexane (85%) mixture as the eluent to afford 4-chloro-2-{4-[2-(5-methyl-2-phenyl-oxazol-4-yl)-ethoxy]-benzenesulfonyl-(t-butoxycarbonyl)amino}benzoic acid methyl ester as a white foam.

H. 4-Chloro-2-{4-[2-(5-methyl-2-phenyl-oxazol-4-yl)-ethoxy]-benzenesulfonyl-amino}-benzoic acid A solution of the title G compound, 4-chloro-2-{4-[2-(5-methyl-2-phenyl-oxazol-4-yl)-ethoxy]-benzenesulfonyl-(t-butoxycarbonyl)amino}-benzoic acid methyl ester (300 mg, 0.48 mmol) in dioxane (5 mL) to which 2.4 mL of 1 N aqueous NaOH is added is heated at 90° C. for 3 h. The mixture is concentrated under vacuum, acidified with 1 N aqueous HCl, and extracted twice with EtOAc. The organic solution is dried over anhydrous magnesium sulfate, filtered and concentrated to give a crude product which is triturated with DCM. The solid is collected by filtration to afford 4-chloro-2-{4-[2-(5-methyl-2-phenyl-oxazol-4-yl)-ethoxy]-benzenesulfonyl-amino}-benzoic acid: m.p. 223-225° C.; ESI-MS 513 [M+1]$^+$.

Example 3

2-[4-(5-Methyl-2-phenyl-oxazol-4-ylmethylsulfanyl)-benzenesulfonylamino]-benzoic acid

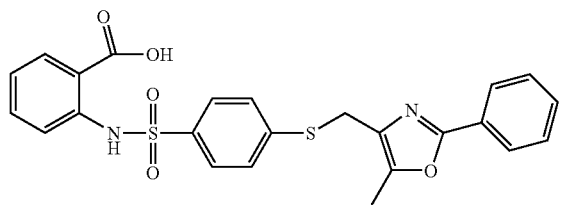

A. 2-(4-Dimethylcarbamoylsulfanyl-benzenesulfonylamino)-benzoic acid methyl ester Dimethylthiocarbamoyl chloride (804 mg, 6.53 mmol) is added to a solution of the title E compound in Example 2, 2-[(4-hydroxybenzenesulfonyl)-(t-butoxycarbonyl)amino] 4-chloro-benzoic acid methyl ester (2.42 g, 5.94 mmol) in 30 mL of DMF, followed by addition of cesium carbonate (3.87 g, 11.88 mmol). The mixture is stirred overnight at RT, and is then partitioned between EtOAc and water. The organic phase is washed with brine, dried over anhydrous magnesium sulfate, filtered, and concentrated to give the crude product. The product is purified by chromatography on silica gel (Biotage 40 M column) using an EtOAc (20%)-hexane (80%) mixture as the eluent to give a thiocarbamate intermediate as a white foam. The thiocarbamate is heated at 200° C. for 5 h, cooled and chromatography on silica gel using a 30% EtOAc in hexane as the eluent then affords 2-(4-dimethylcarbamoyl-sulfanyl-benzenesulfonylamino)-benzoic acid methyl ester as a yellow foam.

B. 2-(4-Mercapto-benzenesulfonylamino)-benzoic acid

Nitrogen is bubbled into a suspension of the title A compound, 2-(4-dimethyl-carbamoyl-sulfanyl-benzenesulfonylamino)-benzoic acid methyl ester (1.01 g, 2.54 mmol) in 25 mL of ethylene glycol for 30 min, followed by addition of a solution of 356 mg (6.34 mmol) of potassium hydroxide in 2 mL of water. The mixture is heated at reflux for 2.5 h, then stirred overnight at RT. The mixture is cooled, diluted with ice-water and acidified to pH 1 with 4 N aqueous HCl (precipitate formed). This mixture is extracted with EtOAc, and the organic phase is washed with brine, dried over anhydrous magnesium sulfate, filtered, and concentrated to give crude product as a white solid. The material so obtained is chromatographed on silica gel using 30% EtOAc in hexane (containing 0.5% formic acid) as the eluent to provide 2-(4-mercaptobenzene-sulfonyl-amino)-benzoic acid.

C. 2-[4-(5-Methyl-2-phenyl-oxazol-4-ylmethylsulfanyl)-benzenesulfonylamino]-benzoic acid A mixture of the title B compound, 2-(4-mercaptobenzenesulfonylamino)-benzoic acid (200 mg, 0.65 mmol), 4-chloromethyl-5-methyl-2-phenyl-oxazole (134 mg, 0.65 mmol) and cesium carbonate (1.05 g, 3.24 mmol) in DMF is stirred at RT for 3 h. The mixture is then partitioned between EtOAc and 1 N aqueous HCl. The organic phase is dried over anhydrous magnesium sulfate, filtered, and concentrated under vacuum. The residue is chromatographed on silica gel using 15% EtOAc in hexane (containing 0.5% formic acid) as the eluent to afford 2-[4-(5-methyl-2-phenyl-oxazol-4-ylmethylsulfanyl)-benzenesulfonyl-amino]-benzoic acid as a white foam: m.p. 182-184° C.; ESI-MS 481 [M+1]$^+$.

Example 4

The following compounds are prepared according to methods described herein above in Example 1, 2 and 3:

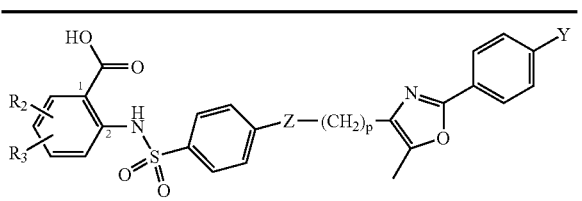

| Compd | R₂ | R₃ | Z | p | Y | m.p. °C. | MS [m/z] |
|---|---|---|---|---|---|---|---|
| 4-1 | 6-Cl | H | O | 1 | H | 170-172 | 497 [M − 1]⁻ |
| 4-2 | H | 4-Ph | O | 1 | H | 75-77 | 541 [M + 1]⁺ |
| 4-3 | H | 4-Cl | O | 1 | CF₃ | 191-193 | 565 [M + 1]⁺ |
| 4-4 | 6-F | H | O | 1 | H | 203-205 | 483 [M + 1]⁺ |
| 4-5 | H | 4-Cl | O | 1 | F | 223-225 | 515 [M + 1]⁺ |
| 4-6 | 6-CF₃ | H | O | 1 | H | 197-198 | 533 [M + 1]⁺ |
| 4-7 | H | 4-Cl | O | 1 | H | 98-100 | 497 [M + 1]⁺ |
| 4-8 | H | H | O | 1 | CF₃ | 195-195 | 533 [M + 1]⁺ |
| 4-9 | H | H | O | 1 | F | 201-203 | 483 [M + 1]⁺ |
| 4-10 | H | 4-F | O | 1 | H | 212-214 | 483 [M + 1]⁺ |
| 4-11 | H | H | O | 1 | H | 195-198 | 465 [M + 1]⁺ |
| 4-12 | H | 4-Me | O | 1 | H | 207-208 | 479 [M + 1]⁺ |
| 4-13 | 6-OMe | H | O | 1 | H | glass | 495 [M + 1]⁺ |
| 4-14 | H | 5-F | O | 1 | H | 213-215 | 483 [M + 1]⁺ |
| 4-15 | H | 5-Cl | O | 1 | H | 207-208 | 499 [M + 1]⁺ |
| 4-16 | H | 5-MeO | O | 1 | H | 190-194 | 495 [M + 1]⁺ |
| 4-17 | H | 5-Me | O | 1 | H | 185-187 | 479 [M + 1]⁺ |
| 4-18 | H | 5-NHCOMe | O | 1 | H | 89-90 | 522 [M + 1]⁺ |
| 4-19 | H | 4-Ph | O | 2 | H | 177-179 | 553 [M + 1]⁺ |
| 4-20 | 6-MeO | 5-MeO | O | 2 | H | 59-60 | 539 [M + 1]⁺ |
| 4-21 | H | H | O | 2 | H | 136-138 | 479 [M + 1]⁺ |
| 4-22 | H | H | S | 2 | H | 200-201 | 496 [M + 1]⁺ |
| 4-23 | 5-F | 4-F | O | 1 | H | 213-215 | 496 [M + 1]⁺ |
| 4-24 | 5-MeO | 4-MeO | O | 1 | H | 206-207 | 525 [M + 1]⁺ |
| 4-25 | 5-Me | 3-Me | O | 1 | H | 165-166 | 493 [M + 1]⁺ |
| 4-26 | 4,5-CH=CH—CH=CH— | | O | 1 | H | 234-236 | 515 [M + 1]⁺ |

Example 5

The following compounds are prepared according to methods described herein above in Example 1 and 2:

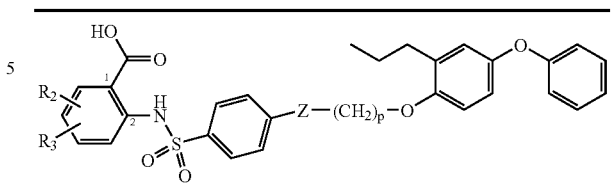

| Compd | R₂ | R₃ | Z | p | m.p. °C. | MS [m/z] |
|---|---|---|---|---|---|---|
| 5-1 | H | H | O | 2 | 135-137 | 546 [M + 1]⁺ |
| 5-2 | 6-MeO | 5-MeO | O | 2 | 101-102 | 608 [M + 1]⁺ |
| 5-3 | H | 4-Cl | O | 2 | 182-184 | 582 [M + 1]⁺ |
| 5-4 | H | H | O | 3 | 36-38 | 563 [M + 1]⁺ |
| 5-5 | H | 4-Ph | O | 3 | 145-147 | 638 [M + 1]⁺ |

Example 6

2-(4-Phenethylcarbamoyl-benzenesulfonylamino)-benzoic acid

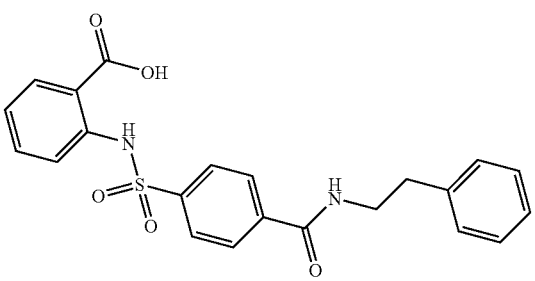

A Methyl 2-(4-carboxybenzenesulfonylamino)-benzoate

4-Chlorosulfonylbenzoic acid (2.21 g, 10 mmol) is added to a solution of the methyl anthranilate (1.51 g, 10 mmol) in 20 mL of DCM at RT. The reaction is stirred 16 h and then filtered to give a white solid. The solid is dissolved in diluted aqueous potassium carbonate and extracted with EtOAc. The aqueous phase is added slowly to an excess (25 mL) of 1 N aqueous HCl. A white solid precipitates and is collected by filtration, washed with water, and dried under vacuum to give methyl 2-(4-carboxybenzene-sulfonylamino)-benzoate.

B. 2-(4-Phenethylcarbamoyl-benzenesulfonylamino)-benzoic acid methyl ester

EDCI (84.4 mg, 0.44 mmol) is added to a solution of the title A compound, followed by methyl 2-(4-carboxy-benzene-sulfonylamino)-benzoate (134.1 mg, 0.40 mmol) and 1-hydroxy-7-azabenzotriazole (HOAt, 59.9 mg, 0.44 mmol) in 1 mL of DMF at RT. The reaction is stirred 1 h after which phenethylamine (50.2 µL, 0.40 mmol) is added. The resulting solution is stirred overnight at RT, followed by addition of 5% aqueous sodium bicarbonate (1 mL) and water (8 mL). A white precipitate is collected by filtration, washed with water, and dried under vacuum to give 2-(4-phenethylcarbamoyl-benzenesulfonyl-amino)-benzoic acid methyl ester m.p. 167-168° C.

C. 2-(4-Phenethylcarbamoyl-benzenesulfonylamino)-benzoic acid

A solution of 1 N aqueous lithium hydroxide (0.78 mL) is added to a solution of the title B compound, 2-(4-phenethylcarbamoyl-benzenesulfonylamino)-benzoic acid methyl ester (113.8 mg, 0.259 mmol) in 4 mL of THF. The reaction is stirred overnight at RT. The solvent is evaporated under a stream of nitrogen, and the residue is partitioned between water (6 mL) and EtOAc. The aqueous layer is washed with EtOAc (1 mL) and then acidified by adding it to a stirred solution of 1 N aqueous HCl (25 mL) to form a white solid. The solid is collected by filtration, washed with water, and dried under vacuum to give 2-(4-phenethylcarbamoyl-benzenesulfonylamino)-benzoic acid: m.p. 242-244° C.; ESI-MS 439.04 [M+1]⁺.

Example 7

2-{(4-[2-(4-Fluoro-phenyl)-ethylcarbamoyl]-benzenesulfonylamino}-benzoic acid

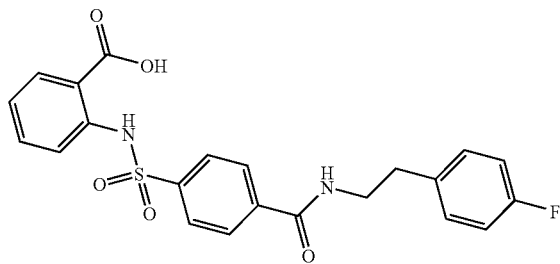

A. 4-Chlorosulfonyl-benzoyl chloride

Oxalyl chloride (1.179 g, 9.29 mmol) is added to a suspension of 4-chlorosulfonyl-benzoic acid (1.025 g, 4.64 mmol) in 10 mL of DCM at RT. A drop of DMF is added. Stirring is continued for 2.5 days. A pale yellow solution results. The reaction mixture is concentrated under vacuum. Toluene is added and the mixture is concentrated under vacuum again. This last process is repeated twice more, and the mixture is finally dried under vacuum to give 4-chlorosulfonyl-benzoyl chloride as a pale yellow solid.

B. 4-[2-(4-Fluoro-phenyl)-ethylcarbamoyl]-benzenesulfonyl chloride

TEA (474 µL, 3.4 mmol), is added dropwise to a suspension of the title A compound, 4-chlorosulfonyl-benzoyl chloride in DCM (10 mL) at −78° C. To this mixture is added p-fluorophenethylamine over 5 min. After another 10 min at −78° C., the solution is allowed to warm to 0° C. and stirring is continued at this temperature for 1 h. The reaction is quenched by adding it to ice-water (30 mL), and the mixture is extracted with DCM (3×10 mL). The combined organic phases are dried over anhydrous magnesium sulfate, filtered, and concentrated under vacuum to obtain the crude product which is chromatographed on silica gel using EtOAc as the eluent to give 4-[2-(4-fluoro-phenyl)-ethylcarbamoyl]-benzenesulfonyl chloride.

C. 2-{4-[2-(4-Fluoro-phenyl)-ethylcarbamoyl]-benzenesulfonylamino}-benzoic acid A solution of the title B compound, 4-[2-(4-fluoro-phenyl)-ethylcarbamoyl]-benzene-sulfonyl chloride (171 mg, 0.5 mmol) in THF (2 mL) is added dropwise over 10 min to a solution of the anthranilic acid (68.6 mg, 0.5 mmol) in water (1 mL) containing sodium bicarbonate (126 mg, 1.5 mmol). After stirring for 30 min, the solvent is evaporated under a stream of nitrogen, and water (8 mL) is added. The mixture is stirred for a few min, then filtered. The filtrate is added dropwise to an excess of 1 N aqueous HCl to precipitate a light tan solid. The solid is collected by filtration, washed with water, and dried under vacuum to give 2-{4-[2-(4-fluoro-phenyl)-ethylcarbamoyl]-benzenesulfonylamino}-benzoic acid: m.p. 85-86° C.; ESI-MS 441 [M−1]⁻.

Example 8

The following compounds are prepared according to methods described herein above in Example 6 and 7:

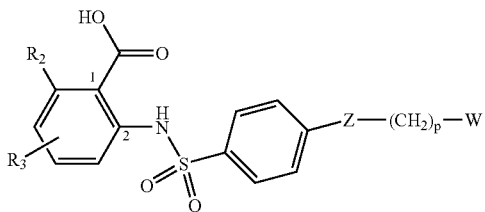

| Compd | $R_2$ | $R_3$ | Z | p | W | m.p. ° C. | MS [m/z] |
|---|---|---|---|---|---|---|---|
| 6-1 | H | H | —C(O)NH— | 1 | F₃C-⟨phenyl⟩- | 330-335 | 479 [M + 1]⁺ |
| 6-2 | H | 4-F | —C(O)NH— | 2 | F-⟨phenyl⟩- | 66-67 | 461 [M + 1]⁺ |

-continued

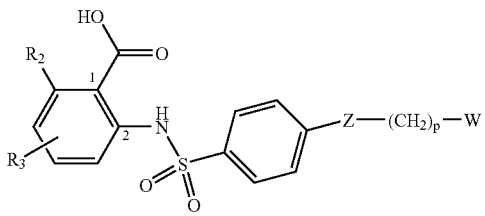

| Compd | $R_2$ | $R_3$ | Z | p | W | m.p. °C. | MS [m/z] |
|---|---|---|---|---|---|---|---|
| 6-3 | H | 4-Cl | —C(O)NH— | 2 | (4-F-phenyl) | 99-106 | 475 [M − 1]⁻ |

Example 9

2-{4-[2-(4-Ethoxy-phenyl)-acetylamino]-benzenesulfonylamino}-benzoic acid

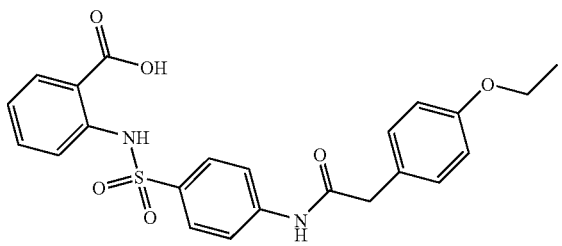

A. 2-(4-Nitro-benzenesulfonylamino)-benzoic acid methyl ester

4-Nitrobenzenesulfonyl chloride (2.22 g, 10 mmol) is added to a solution of methyl anthranilate (1.51 g, 10 mmol) in 20 mL of DCM at RT, followed by slow addition of pyridine (0.97 mL, 12 mmol). The reaction is stirred 16 h at RT. Water (1 mL) is added. After 1 h, the mixture is partitioned between DCM (40 mL) and water (30 mL). The organic phase is washed with water (30 mL) and brine (30 mL), dried over anhydrous magnesium sulfate and concentrated under vacuum to an orange solid. The solid is redissolved in DCM (30 mL), and hexane (100 mL) is added. The solution is concentrated to approximately 60 mL at which point an orange solid rapidly precipitated. The solid is collected by filtration and dried under vacuum to give 2-(4-nitro-benzenesulfonylamino)-benzoic acid methyl ester.

B. 2-(4-Amino-benzenesulfonylamino)-benzoic acid methyl ester

A solution of the title A compound, 2-(4-nitro-benzenesulfonylamino)-benzoic acid methyl ester (1 g, 2.98 mmol) in 40 mL of ethanol containing 0.32 g of 10% palladium on carbon is shaken under 40 psi of hydrogen pressure at RT for 2.5 h. The mixture is filtered and concentrated under vacuum to give 2-(4-amino-benzenesulfonyl-amino)-benzoic acid methyl ester.

C. 2-{4-[2-(4-Ethoxy-phenyl)-acetylamino]-benzenesulfonylamino}-benzoic acid methyl ester EDCI (119.5, 0.623 mmol) is added to a solution of the acid (102.1 mg, 0.567 mmol) and HOAt (84.8 mg, 0.623 mmol) in 1 mL of DMF at RT. The reaction is stirred 1 h after which the title B compound, 2-(4-amino-benzenesulfonylamino)-benzoic acid methyl ester (173.6, 0.567 mmol) is added. The resulting solution is stirred overnight at RT, followed by addition of 5% aqueous sodium bicarbonate (1 mL) and water (8 mL). A white precipitate is collected by filtration, washed with water, and dried under vacuum to give 298.1 mg of product as a tan glass. The product is chromatographed on a silica gel column using 40% EtOAc in hexane as the eluent to give the product as a glass. This material is dissolved in 2 mL of DCM, diluted with 3 mL of t-butyl methyl ether, and treated with 0.18 g of p-toluenesulfonic acid. The resulting mixture is stirred for 1 h and filtered. Concentration of the filtrate under vacuum gives 2-{4-[2-(4-ethoxy-phenyl)-acetylamino]benzenesulfonyl-amino}benzoic acid methyl ester.

D. 2-{4-[2-(4-Ethoxy-phenyl)-acetylamino]-benzenesulfonylamino}-benzoic acid The title D compound, 2-{4-[2-(4-ethoxy-phenyl)-acetylamino]-benzenesulfonyl-amino}-benzoic acid methyl ester (189.1 mg, 0.356 mmol) is dissolved in 4 mL of THF and 1.07 mL of 1 N aqueous lithium hydroxide is added. The mixture is stirred at RT for 3 days and is then concentrated under a stream of nitrogen. The residue is taken up in warm water (20 mL) to give a clear solution. The solution is added slowly to 30 mL of 1 N aqueous HCl. The resulting precipitate is collected by filtration, washed with water, and dried under vacuum to give 2-{4-[2-(4-ethoxy-phenyl)-acetylamino] benzenesulfonylamino}benzoic acid: m.p. 241-242° C.: ESI-MS 455 [M+1]⁺.

Example 10

2-Methyl-6-[4-(5-methyl-2-phenyl-oxazol-4-yl-methoxy)-benzyloxy]-4-propoxy-benzoic acid methyl ester

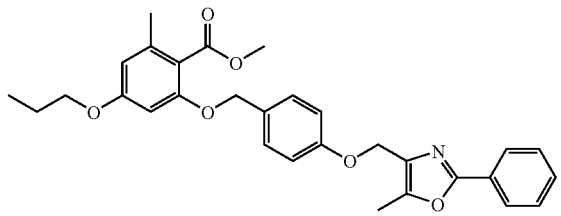

A. 2-Hydroxy-6-methyl-4-propoxy-benzoic acid methyl ester

A mixture of 1-iodopropane (1.87 g, 10.98 mmol), methyl orsellinate (2.0 g, 10.98 mmol), and sodium bicarbonate (1.84 g, 21.96 mmol) in DMF is stirred at 60° C. overnight. The mixture is cooled and partitioned between EtOAc and water. The EtOAc layer is washed with brine, dried over magnesium sulfate, and concentrated to give the crude product. Purification by silica gel chromatography using 2% EtOAc in hexane as the eluent gives 2-hydroxy-6-methyl-4-propoxy-benzoic acid methyl ester.

B. 4-(5-Methyl-2-phenyl-oxazol-4-ylmethoxy)-benzoic acid methyl ester

A mixture of 4-chloromethyl-5-methyl-2-phenyl-oxazole (3.0 g, 14.4 mmol), methyl 4-hydroxybenzoate (2.64 g, 17.3 mmol), and potassium carbonate (6.0 g, 43.34 mmol) in DMF is stirred at RT overnight. The mixture is then partitioned between EtOAc and water, and the organic phase is washed with brine, dried over magnesium sulfate, and concentrated under vacuum to give the crude product. The material is purified by silica gel chromatography using 15% EtOAc in hexane as the eluent to give 4-(5-methyl-2-phenyl-oxazol-4-ylmethoxy) benzoic acid methyl ester as a white solid.

C. [4-(5-Methyl-2-phenyl-oxazol-4-ylmethoxy)-phenyl]-methanol

Lithium aluminum hydride (15.5 mL of a 1.0 M solution in THF) is added slowly to a cooled (ice-water bath) solution of the title B compound, 4-(5-methyl-2-phenyl-oxazol-4-yl-methoxy)-benzoic acid methyl ester (2.0 g, 6.18 mmol) in THF (30 mL). The mixture is stirred at 0° C. for 3 h, then quenched with saturated sodium bicarbonate, and extracted with EtOAc. The organic solution is washed with brine, dried over magnesium sulfate, and concentrated under vacuum to give the crude product. The product is purified by silica gel chromatography using 30% EtOAc in hexane as the eluent to give [4-(5-methyl-2-phenyl-oxazol-4-ylmethoxy)-phenyl]-methanol as a white solid.

D. 4-(4-Bromomethyl-phenoxymethyl)-5-methyl-2-phenyl-oxazole

A mixture of the title C compound, [4-(5-methyl-2-phenyl-oxazol-4-ylmethoxy)-phenyl]-methanol (1.5 g, 5.08 mmol), carbon tetrabromide (2.53 g, 7.62 mmol), and triphenylphosphine (2.0 g, 7.62 mmol) in DCM is stirred at RT overnight. The mixture is then concentrated under vacuum, and chromatographed on a silica gel column using 8% EtOAc in hexane as the eluent to give 4-(4-bromomethyl-phenoxymethyl)-5-methyl-2-phenyl-oxazole as a white solid.

E. 2-Methyl-6-[4-(5-methyl-2-phenyl-oxazol-4-yl-methoxy)-benzyloxy]4-propoxy-benzoic acid methyl ester A mixture of the title A compound, 2-hydroxy-6-methyl-4-propoxy-benzoic acid methyl ester (407 mg, 1.81 mmol), the title D compound, 4-(4-bromomethyl-phenoxymethyl)-5-methyl-2-phenyl-oxazole (650 mg, 1.81 mmol) and potassium carbonate (751 mg, 5.44 mmol) in DMF is stirred at RT overnight. The mixture is then partitioned between EtOAc and water. The organic layer is washed with brine, dried with magnesium sulfate and concentrated under vacuum to give the crude product. Chromatography on silica gel, using 10% EtOAc in hexane gives 2-methyl-6-[4-(5-methyl-2-phenyl-oxazol-4-ylmethoxy)-benzyloxy]-4-propoxy-benzoic acid methyl ester as a white foam: ESI-MS 502 [M+1]+.

Example 11

4-Methoxy-2-{4-[2-(5-methyl-2-phenyl-oxazol-4-yl)-ethoxy]-benzyloxy}-benzoic acid

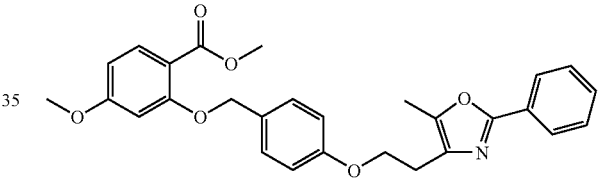

A. 5-Methyl-2-phenyl-4-(2-p-tolyloxy-ethyl)-oxazole

Di-t-butylazodicarboxylate (9.46 g, 41.08 mmol) is added to a stirred solution of triphenylphosphine (10.77 g, 41.08 mmol), 2-(5-methyl-2-phenyl-oxazol-4-yl)-ethanol (7.35 g, 36.15 mmol) and methyl 4-hydroxybenzoate (5.0 g, 32.86 mmol) in toluene (120 mL) at 0° C. After stirring for 15 min, the ice-water bath is removed. Stirring is continued for 1 h at RT, 1 h at 40° C., and overnight at RT. The reaction is then concentrated under vacuum, and the residue is crystallized from EtOAc to give 5-methyl-2-phenyl-4-(2-p-tolyloxy-ethyl)-oxazole as a white solid.

B. {4-[2-(5-Methyl-2-phenyl-oxazol-4-yl)-ethoxy]-phenyl}-methanol

Lithium aluminum hydride (61 mL of a 1.0 M solution in THF) is added to a solution of the title A compound, 5-methyl-2-phenyl-4-(2-p-tolyloxy-ethyl)-oxazole (8.22 g, 24.36 mmol) in THF (200 mL) at 0° C. The mixture is stirred at 0° C. for 5 h, then at RT overnight. The reaction mixture is then cooled in an ice-water bath and quenched with saturated aqueous sodium bicarbonate and concentrated under vacuum to remove some of the THF. The residue is extracted with EtOAc, and the resulting organic phase is washed with brine, dried with magnesium sulfate, and concentrated under vacuum to give {4-[2-(5-methyl-2-phenyl-oxazol-4-yl)-ethoxy]-phenyl}-methanol as a white solid.

C. 4-[2-(4-Bromomethyl-phenoxy)-ethyl]-5-methyl-2-phenyl-oxazole

Triphenylphosphine (2.54 g, 9.7 mmol) is added to a solution of carbon tetrabromide (3.22 g, 9.7 mmol) and the title B compound, {4-[2-(5-methyl-2-phenyl-oxazol-4-yl)-ethoxy]-phenyl}-methanol (2.0 g, 6.46 mmol) in DCM (24 mL) at RT. The mixture is stirred overnight and then concentrated under vacuum. The residue is chromatographed on silica gel using 15% EtOAc in hexane as the eluent to provide 4-[2-(4-bromomethyl-phenoxy)-ethyl]-5-methyl-2-phenyl-oxazole as a white solid.

D. 4-Methoxy-2-{4-[2-(5-methyl-2-phenyl-oxazol-4-yl)-ethoxy]-benzyloxy}-benzoic acid methyl ester A mixture of methyl 4-methoxysalicylate (176 mg, 0.97 mmol), the title C compound, 4-[2-(4-bromomethyl-phenoxy)-ethyl]-5-methyl-2-phenyl-oxazole (300 mg, 0.81 mmol) and potassium carbonate (334 mg, 2.42 mmol) in DMF (10 mL) is stirred at RT overnight. The mixture is partitioned between EtOAc and water. The organic phase is washed with brine, dried over magnesium sulfate, and concentrated. The residue is chromatographed on silica gel using 15% EtOAc in hexane as the eluent to give 4-methoxy-2-{4-[2-(5-methyl-2-phenyl-oxazol-4-yl)-ethoxy]-benzyloxy}-benzoic acid methyl ester.

E. 4-Methoxy-2-{4-[2-(5-methyl-2-phenyl-oxazol-4-yl)-ethoxy]-benzyloxy}-benzoic acid The title D compound, 4-methoxy-2-{4-[2-(5-methyl-2-phenyl-oxazol-4-yl)-ethoxy]-benzyloxy}-benzoic acid methyl ester (220 mg, 0.46 mmol) is taken up in 5 mL of 1,4-dioxane and 1.4 mL of 1 N aqueous NaOH is added. The solution is stirred overnight at RT, followed by 5 h at 90° C. The mixture is concentrated under vacuum, and the residue is acidified (4 N HCl) and extracted with EtOAc. The organic phase is washed with brine, dried over magnesium sulfate, and concentrated to give 4-methoxy-2-{4-[2-(5-methyl-2-phenyl-oxazol-4-yl)-ethoxy]-benzyloxy}benzoic acid: m.p. 113-115° C.; ESI-MS 460 [M+1]+.

Example 12

2-Methyl-6-{4-[2-(5-methyl-2-phenyl-oxazol-4-yl)-ethoxy]-benzyloxy}-4-propoxy-benzoic acid methyl ester

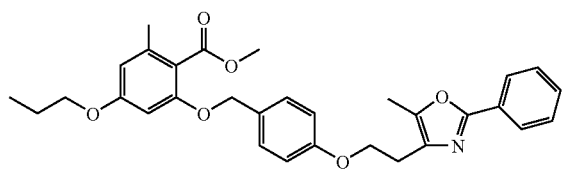

The title compound is prepared analogously to Example 11: ESI-MS 516 [M+1]+.

Example 13

4-Chloro-2-{4-[2-(5-methyl-2-phenyl-oxazol-4-yl)-ethoxy]-benzyloxy}-benzoic acid ethyl ester

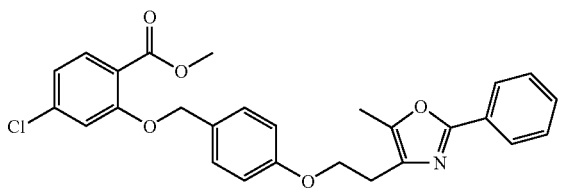

The title compound is prepared analogously to Example 11: ESI-MS 490 [M+1]+.

Example 14

3-{4-[2-(5-Methyl-2-phenyl-oxazol-4-yl)-ethoxy]-benzyloxy}-naphthalene-2-carboxylic acid

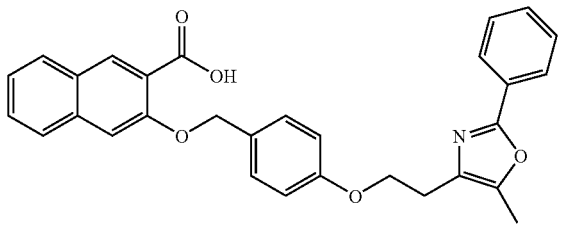

The title compound is prepared analogously to Example 11: m.p. 135-137° C.; ESI-MS 480 [M+1]+.

Example 15

2-{4-[2-(5-Methyl-2-phenyl-oxazol-4-yl)-ethoxy]-benzyloxy}-4-propoxy-benzoic acid

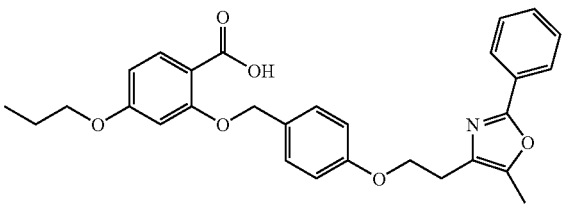

The title compound is prepared analogously to Example 11: m.p. 108-109° C.; ESI-MS 488 [M+1]+.

Example 16

4-Methyl-2-{4-[2-(5-methyl-2-phenyl-oxazol-4-yl)-ethoxy]-benzyloxy}-benzoic acid

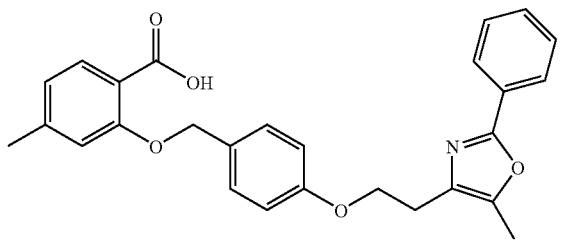

The title compound is prepared analogously to Example 11: m.p. 116-118° C.; ESI-MS 440 [M+1]+.

Example 17

4-Chloro-2-[3-(5-methyl-2-phenyl-oxazol-4-yl-methoxy)-benzyloxy]-benzoic acid

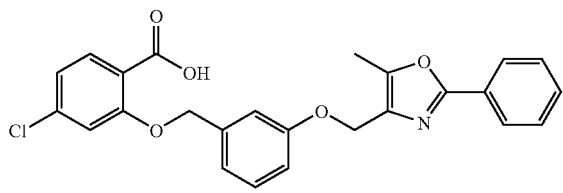

The title compound is prepared analogously to Example 11: m.p. 168° C.; ESI-MS 448 [M−1]−.

Example 18

4-Chloro-2-[3-(5-methyl-2-phenyl-oxazol-4-yl-methoxymethyl)-benzyloxy]-benzoic acid

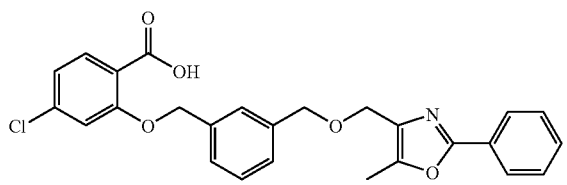

The title compound is prepared analogously to Example 11: m.p. 137° C.; ESI-MS 462 [M−1]−.

Example 19

2-Methyl-6-{4-[2-(5-methyl-2-phenyl-oxazol-4-yl)-ethoxy]-benzyloxy}-4-propoxy-benzoic acid

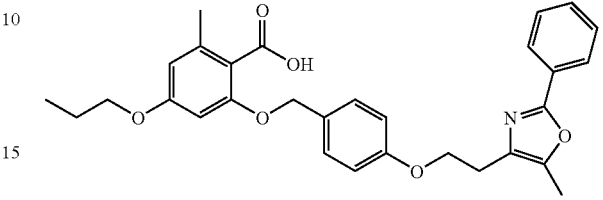

A. Orsellinic Acid Sodium Salt

Orsellinic acid (1.65 g, 8.86 mmol) is dissolved in 8.4 mL of 1 N aqueous NaOH with slight warming. The solution is then concentrated to dryness under vacuum to give orsellinic acid sodium salt as a dry powder.

B. Orsenillic Acid Allyl Ester

The title A compound, orsenillic acid sodium salt (8.86 mmol) is then stirred with allyl bromide (1.39 g, 11.49 mmol) in 15 mL of DMF at RT overnight. The mixture is acidified and partitioned between EtOAc and water. The organic layer is washed with brine, dried over magnesium sulfate, and concentrated to give the crude product. This product was purified on silica gel chromatography using 15% EtOAc in hexane as the eluent to give orsenillic acid allyl ester as a white solid.

C. 2-Hydroxy-6-methyl-4-propoxy-benzoic acid allyl ester

A mixture of the title B compound, orsenillic acid allyl ester (500 mg, 2.4 mmol), 1-iodopropane (531 mg, 3.12 mmol) and sodium bicarbonate (605 mg, 7.2 mmol) is stirred in 10 mL of DMF at 60° C. overnight. The mixture is partitioned between EtOAc and brine. The organic layer was washed with brine, dried over magnesium sulfate, and concentrated to give the crude product which is purified by silica gel chromatography using 10% EtOAc in hexane as the eluent to give 2-hydroxy-6-methyl-4-propoxy-benzoic acid allyl ester as an oil.

D. 2-Methyl-6-{4-[2-(5-methyl-2-phenyl-oxazol-4-yl)-ethoxy]-benzyloxy}-4-propoxy-benzoic acid allyl ester A mixture of the title C compound, 2-hydroxy-6-methyl-4-propoxy-benzoic acid allyl ester (400 mg, 1.6 mmol), the title C compound in Example 11, 4-[2-(4-bromomethyl-phenoxy)-ethyl]-5-methyl-2-phenyl-oxazole (595 mg, 1.6 mmol) and potassium carbonate (662 mg, 4.79 mmol) in 15 mL of DMF is stirred at RT overnight. The mixture is partitioned between EtOAc and water. The organic phase is washed with brine, dried over magnesium sulfate, and concentrated under vacuum. The residue is chromatographed on silica gel using 15% EtOAc in hexane as the eluent to obtain 2-methyl-6-{4-[2-(5-methyl-2-phenyl-oxazol-4-yl)-ethoxy]-benzyloxy}4-propoxy-benzoic acid allyl ester as an oil: ESI-MS 542 [M+1]⁺.

E. 2-Methyl-6-{4-[2-(5-methyl-2-phenyl-oxazol-4-yl)-ethoxy]-benzyloxy}-4-propoxy-benzoic acid A mixture of the title D compound, 2-methyl-6-{4-[2-(5-methyl-2-phenyl-oxazol-4-yl)-ethoxy]-benzyloxy}-4-propoxy-benzoic acid allyl ester (620 mg, 1.16 mmol), tetrakis-(triphenyl-phosphine)palladium(0) (27 mg, 0.02 equivalents), and phenyl silane (252 mg, 2.33 mmol) in DCM (15 mL) is stirred at RT for 4 h. The mixture is concentrated under vacuum, and the residue is chromatographed on silica gel using a solvent mixture consisting of 0.5% formic acid and 20% ethyl acetate in hexane as the eluent to afford 2-methyl-6-{4-[2-(5-methyl-2-phenyl-oxazol-4-yl)-ethoxy]-benzyloxy}-4-propoxy-benzoic acid as a white foam: m.p. 50-52° C.

Example 20

4-Isopropoxy-2-methyl-6-{(3-[2-(5-methyl-2-phenyl-oxazol-4-yl)-ethoxy]-benzyloxy}-benzoic acid

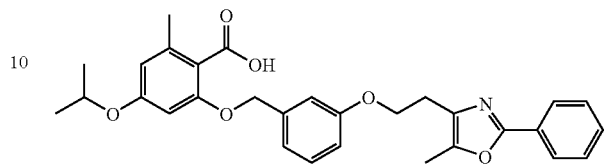

The title compound is prepared analogously to Example 19: ESI-MS 500 [M−1]⁻.

Example 21

The following compounds are prepared according to methods described herein in the above examples or using methods generally known in the art:

| Compd | R₂ | R₃ | Z | p | Q | R″ | m.p. ° C. | MS [m/z] |
|---|---|---|---|---|---|---|---|---|
| 21-1 | MeO | MeO | O | 2 | bond | H | 58-60 | 490 (M + 1)⁺ |
| 21-2 | MeO | MeO | O | 1 | bond | H | 182-183 | 476 [M + 1]⁺ |
| 21-3 | Me | n-PrO | O | 1 | bond | H | 182-183 | 488 [M + 1]⁺ |
| 21-4 | CF₃ | CF₃ | O | 2 | bond | H | 162-163 | |
| 21-5 | CF₃ | CF₃ | O | 1 | bond | H | 190-191 | |
| 21-6 | F | H | O | 1 | bond | H | 167-168 | 451 [M + NH₄]⁺ |
| 21-7 | Me | i-PrO | O | 2 | bond | H | 157-158 | 502 [M + 1]⁺ |
| 21-8 | F | H | O | 2 | bond | H | 142-143 | 448 [M + 1]⁺ |
| 21-9 | MeO | H | O | 1 | bond | H | 180-181 | 446 [M + 1]⁺ |
| 21-10 | MeO | H | O | 2 | bond | H | 183-184 | 460 [M + 1]⁺ |
| 21-11 | H | Cl | O | 1 | bond | H | 155-156 | 448 [M − 1]⁺ |
| 21-12 | H | Cl | O | 2 | bond | H | 148-149 | |
| 21-13 | Me | s-BuO | O | 2 | bond | F | | 532 [M − 1]⁻ |
| 21-14 | i-PrO | F | O | 2 | bond | F | | 522 [M − 1]⁻ |
| 21-15 | n-PrO | F | O | 2 | bond | F | | 522 [M − 1]⁻ |
| 21-16 | Me | i-PrO | O | 2 | bond | F | | 518 [M − 1]⁻ |
| 21-17 | Me | i-PrO | O | 2 | bond | CF₃ | | 568 [M − 1]⁻ |
| 21-18 | Me | (tetrahydrofuran-3-yl)oxy | O | 2 | bond | F | | 546 [M − 1]⁻ |
| 21-19 | H | Cl | bond | 1 | OCH₂ | H | 151 | 462 [M − 1]⁻ |

Example 22

The following compounds are prepared according to methods described herein in the above examples or using methods generally known in the art:

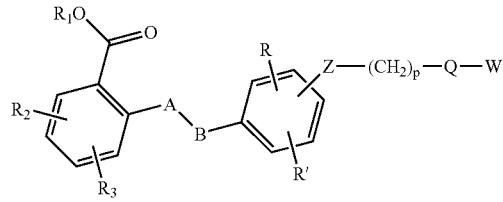

| Compd | R₂ | R₃ | R₆ | W | MS [m/z] |
|---|---|---|---|---|---|
| 22-1 | H | Cl | H | 2-phenyl-4-methylthiazol-5-yl | 491 [M − 1]⁻ |
| 22-2 | Me | i-PrO | Me | 4-(trifluoromethyl)benzyl | 528 [M − 1]⁻ |
| 22-3 | Me | i-PrO | Et | 4-(trifluoromethyl)benzyl | 542 [M − 1]⁻ |
| 22-4 | Me | i-PrO | Me | 4-chlorobenzyl | 494 [M − 1]⁻ |
| 22-5 | Me | i-PrO | Me | 4-methylbenzyl | 474 [M − 1]⁻ |
| 22-6 | Me | i-PrO | Me | benzo[1,3]dioxol-5-ylmethyl | 504 [M − 1]⁻ |
| 22-7 | Me | i-PrO | Me | benzyl | 460 [M − 1]⁻ |

The invention claimed is:

1. A compound of the formula

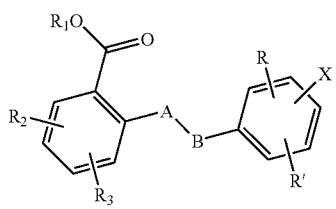

(I)

wherein
- R₁ is hydrogen, optionally substituted alkyl, aryl, heteroaryl, aralkyl or cycloalkyl;
- R₂ and R₃ are independently hydrogen, halogen, hydroxy, cyano, nitro, trifluoromethyl, optionally substituted alkyl, aryl, heteroaryl, aralkyl, heteroaralkyl, alkoxy, aryloxy, aralkoxy or heteroaralkoxy; or
- R₂ and R₃ combined together with the carbon atoms they are attached to form an optionally substituted fused 5- to 6-membered aromatic or heteroaromatic ring provided that R₂ and R₃ are attached to carbon atoms adjacent to each other;
- R and R' are independently hydrogen, halogen, optionally substituted alkyl, alkoxy, aralkyl or heteroaralkyl; or
- R and R' combined together with the carbon atoms to which they are attached form an optionally substituted fused 5- to 6-membered aromatic or heteroaromatic ring provided that R and R' are attached to carbon atoms adjacent to each other; or
- X is —Z—(CH₂)$_p$-Q-W in which
  - Z is O or S;
  - p is an integer from 1 to 8;
  - Q is a bond or
  - Q is —O(CH₂)$_r$— in which
    - r is zero
  - W is cycloalkyl, aryl or heterocyclyl;
- A-B is —NH—S(O)₂—;

or a pharmaceutically acceptable salt thereof.

2. The compound according to claim 1 of the formula (IA)

[structure IA]

wherein
- R₁ is hydrogen or optionally substituted alkyl;
- R₂ and R₃ are independently hydrogen, halogen, trifluoromethyl, optionally substituted lower alkyl, alkoxy, aryl or heteroaryl; or
- R₂ and R₃ combined together with the carbon atoms they are attached to form an optionally substituted fused 5- to 6-membered aromatic or heteroaromatic ring provided that R₂ and R₃ are attached to carbon atoms adjacent to each other
- R and R' are independently hydrogen, halogen, optionally substituted C$_{1-6}$ alkyl, C$_{1-8}$ alkoxy, aralkyl or heteroaralkyl;
- p is an integer from 1 to 5;

or a pharmaceutically acceptable salt thereof.

3. The compound according to claim 2 wherein
- R₂ and R₃ are independently hydrogen, halogen, trifluoromethyl, optionally substituted lower alkyl, alkoxy, aryl or heteroaryl; or
- R₂ and R₃ combined together with the carbon atoms they are attached to form an optionally substituted fused 6-membered aromatic ring provided that R₂ and R₃ are attached to carbon atoms adjacent to each other;
- R is hydrogen, halogen, optionally substituted C$_{1-6}$ alkyl or C$_{1-8}$ alkoxy;
- R' is hydrogen;

or a pharmaceutically acceptable salt thereof.

4. The compound according to claim 3 of the formula

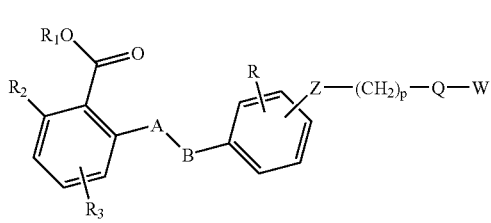
(IB)

wherein
R₂ and R₃ are independently hydrogen, halogen, trifluoromethyl, lower alkyl, lower alkoxy or aryl,
or a pharmaceutically acceptable salt thereof.

5. The compound according to claim 4 of the formula

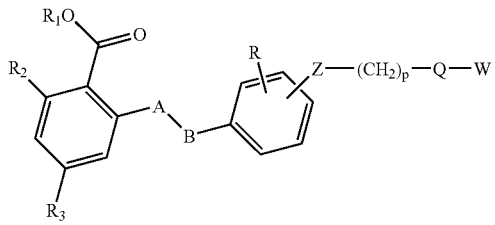
(IC)

wherein
R₁ is hydrogen or optionally substituted lower alkyl;
R₂ and R₃ are independently hydrogen, halogen, lower alkyl or lower alkoxy;
R is hydrogen;
p is an integer from 1 to 4;
or a pharmaceutically acceptable salt thereof.

6. The compound according to claim 5 wherein
R₁ and R₃ are hydrogen;
R₂ is hydrogen, fluoro, chloro, C₁₋₃ alkyl or C₁₋₃ alkoxy;
or a pharmaceutically acceptable salt thereof.

7. The compound according to claim 5 wherein
R₁ is hydrogen;
R₂ is hydrogen, fluoro, chloro, C₁₋₃ alkyl or C₁₋₃ alkoxy;
R₃ is fluoro, chloro, C₁₋₃ alkyl, or C₁₋₃ alkoxy;
or a pharmaceutically acceptable salt thereof.

8. The compound according to claim 5 wherein
p is an integer of 1 or 2;
or a pharmaceutically acceptable salt thereof.

9. The compound according to claim 5 wherein
p is an integer of 2 or 3;
or a pharmaceutically acceptable salt thereof.

10. The compound according to claim 9 wherein W is

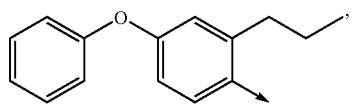

or a pharmaceutically acceptable salt thereof.

11. The compound according to claim 9 wherein W is

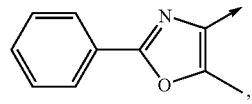

or a pharmaceutically acceptable salt thereof.

12. A compound according to claim 1 which is selected from the group consisting of:
  6-Methyl-2-[4-(5-methyl-2-phenyl-oxazol-4-ylmethoxy)-benzenesulfonylamino]-benzoic acid;
  6-Chloro-2-[4-(5-methyl-2-phenyl-oxazol-4-ylmethoxy)-benzenesulfonylamino]-benzoic acid;
  3-[4-(5-Methyl-2-phenyl-oxazol-4-ylmethoxy)-benzenesulfonylamino]-biphenyl-4-carboxylic acid;
  4-Chloro-2-{4-[5-methyl-2-(4-trifluoromethyl-phenyl)-oxazol-4-ylmethoxy]-benzene-sulfonylamino}-benzoic acid;
  6-Fluoro-2-[4-(5-methyl-2-phenyl-oxazol-4-ylmethoxy)-benzenesulfonylamino]-benzoic acid;
  4-Chloro-2-{4-[2-(4-fluoro-phenyl)-5-methyl-oxazol-4-ylmethoxy]-benzenesulfonylamino}-benzoic acid;
  2-{4-(5-Methyl-2-phenyloxazol-4-ylmethoxy)benzenesulfonylamino}-6-trifluoromethyl-benzoic acid;
  4-Chloro-2-[4-(5-methyl-2-phenyl-oxazol-4-ylmethoxy)-benzenesulfonylamino]-benzoic acid;
  3,5-Dimethyl-2-[4-(5-methyl-2-phenyl-oxazol-4-ylmethoxy)-benzenesulfonylamino]-benzoic acid;
  2-{4-[5-Methyl-2-(4-trifluoromethyl-phenyl)-oxazol-4-ylmethoxy]benzenesulfonylamino}-benzoic acid;
  2-{4-[2-(4-Fluoro-phenyl)-5-methyl-oxazol-4-ylmethoxy]-benzenesulfonylamino}-benzoic acid;
  2-[4-(5-Methyl-2-phenyl-oxazol-4-ylmethylsulfanyl)-benzenesulfonylamino]benzoic acid;
  4-Fluoro-2-[4-(5-methyl-2-phenyl-oxazol-4-ylmethoxy)-benzenesulfonylamino]-benzoic acid;
  2-[4-(5-Methyl-2-phenyl-oxazol-4-ylmethoxy)-benzenesulfonylamino]-benzoic acid;
  4-Methyl-2-[4-(5-methyl-2-phenyl-oxazol-4-ylmethoxy)-benzenesulfonylamino]-benzoic acid;
  4,5-Difluoro-2-[4-(5-methyl-2-phenyl-oxazol-4-ylmethoxy)-benzenesulfonylamino]-benzoic acid;
  6-Methoxy-2-[4-(5-methyl-2-phenyl-oxazol-4-ylmethoxy)-benzenesulfonylamino]-benzoic acid;
  5-Fluoro-2-[4-(5-methyl-2-phenyl-oxazol-4-ylmethoxy)-benzenesulfonylamino]-benzoic acid;
  5-Chloro-2-[4-(5-methyl-2-phenyl-oxazol-4-ylmethoxy)-benzenesulfonylamino]-benzoic acid;
  3-[4-(5-Methyl-2-phenyl-oxazol-4-ylmethoxy)-benzenesulfonylamino]-naphthalene-2-carboxylic acid;
  5-Methoxy-2-[4-(5-methyl-2-phenyl-oxazol-4-ylmethoxy)-benzenesulfonylamino]-benzoic acid;
  5-Methyl-2-[4-(5-methyl-2-phenyl-oxazol-4-ylmethoxy)-benzenesulfonylamino]-benzoic acid;
  5-Acetylamino-2-[4-(5-methyl-2-phenyl-oxazol-4-ylmethoxy)-benzenesulfonylamino]-benzoic acid;
  4,5-Dimethoxy-2-[4-(5-methyl-2-phenyl-oxazol-4-ylmethoxy)-benzenesulfonylamino]-benzoic acid;

4-Chloro-5-{7-[2-(5-methyl-2-phenyl-oxazol-7-yl)-ethoxy]-benzenesulfonylamino}-benzoic acid;

3-{4-[2-(5-Methyl-2-phenyl-oxazol-4-yl)-ethoxy]-benzenesulfonylamino}-biphenyl-4-carboxylic acid;

2,3-Dimethoxy-6-{4-[2-(5-methyl-2-phenyl-oxazol-4-yl)-ethoxy]-benzenesulfonylamino}-benzoic acid;

2-{4-[2-(5-Methyl-2-phenyl-oxazol-4-yl)-ethoxy]-benzenesulfonylamino}-benzoic acid;

2-{4-[2-(5-Methyl-2-phenyl-oxazol-4-yl)-ethylsulfanyl]-benzenesulfonylamino}-benzoic acid;

or a pharmaceutically acceptable salt thereof.

13. A pharmaceutical composition, comprising:
a therapeutically effective amount of a compound of claim 1 in combination with one or more pharmaceutically acceptable carriers.

14. A pharmaceutical composition, comprising:
a therapeutically effective amount of a compound of claim 1 in combination with a therapeutically effective amount of an anti-diabetic agent, a hypolipidemic agent, an anti-obesity agent or an anti-hypertensive agent.

* * * * *